(12) United States Patent
Yeung et al.

(10) Patent No.: US 8,050,881 B1
(45) Date of Patent: Nov. 1, 2011

(54) POST DATA-COLLECTION SYNCHRONIZATION FOR APPROXIMATION OF SIMULTANEOUS DATA

(75) Inventors: King-Wah Walter Yeung, Cupertino, CA (US); Wei-Wei Vivian Yeung, Cupertino, CA (US)

(73) Assignee: Enbiomedic, Cupertino, CA (US)

( * ) Notice: Subject to any disclaimer, the term of this patent is extended or adjusted under 35 U.S.C. 154(b) by 534 days.

(21) Appl. No.: 12/243,702

(22) Filed: Oct. 1, 2008

Related U.S. Application Data

(60) Provisional application No. 60/999,490, filed on Oct. 18, 2007, provisional application No. 61/008,504, filed on Dec. 19, 2007.

(51) Int. Cl.
*G01D 18/00* (2006.01)

(52) U.S. Cl. .......... 702/89; 702/187; 702/188; 370/503; 370/507; 370/510; 370/512; 375/354; 375/356; 375/359; 375/362

(58) Field of Classification Search .............. 702/89, 702/187, 188; 370/503, 507, 510, 512; 375/354, 375/356, 359, 362
See application file for complete search history.

(56) References Cited

U.S. PATENT DOCUMENTS

| | | | |
|---|---|---|---|
| 5,566,180 A | | 10/1996 | Eidson et al. |
| 5,894,450 A | * | 4/1999 | Schmidt et al. ............... 367/134 |
| 6,654,356 B1 | | 11/2003 | Eidson et al. |

OTHER PUBLICATIONS

Zhang, Measurement of Human Daily Physical Activity, Obesity Research, vol. 11, No. 1, 2003, pp. 33-40.
Bao, Activity Recognition from User-Annotated Acceleration Data, Proceedings of the Second International Conference on Pervasive Computing 2004, pp. 1-17.

* cited by examiner

*Primary Examiner* — Sujoy Kundu

(57) ABSTRACT

A system for synchronizing data after they are collected and stored locally in sensor units in a distributed sensor system, so that wired or wireless communication is not required during a data-collection session. Each sensor unit has a local clock providing local-clock times before and after a data-collection session, and a data processor uses its local clock or a sensor unit's local clock as the reference to compute each sensor unit's time-scaling factor, which is the ratio of the elapsed reference local-clock time and the elapsed local-clock time. The data processor uses the time-scaling factor to convert each sensor unit's local-clock data-sampling times to the reference local-clock data-sampling times, and the data processor subsequently interpolates sensor data to approximate simultaneous sensor-data values at desired reference local-clock times. A physical-activity monitoring system can use this synchronization method to reduce the size, power consumption, and cost of the sensor units.

20 Claims, 19 Drawing Sheets

POST DATA-COLLECTION SYNCHRONIZATION FOR APPROXIMATION OF SIMULTANEOUS DATA

CROSS-REFERENCE TO RELATED APPLICATIONS

This application claims the benefit of provisional application Ser. No. 60/999,490, filed 2007 Oct. 18 by the present inventors, and provisional application Ser. No. 61/008,504, filed 2007 Dec. 19 by the present inventors.

FEDERALLY SPONSORED RESEARCH

Not Applicable

SEQUENCE LISTING OR PROGRAM

Not Applicable

BACKGROUND

1. Field

This application relates to time synchronization of data obtained from sensors distributed at different locations, specifically to synchronization of sensor data after they are timestamped with local clocks in a distributed sensor system.

2. Prior Art

In a distributed sensor system that has multiple sensor units at different physical locations, each sensor unit's local clock may be used to schedule sensor-data collection or to timestamp sensor-data samples, and synchronization and syntonization of the local clocks in the distributed sensor system are important for obtaining simultaneous data from the sensors. Clock synchronization sets the clocks to the same time at a given instant, and clock syntonization adjusts the clocks to the same clock frequency.

U.S. Pat. No. 5,894,450 (1999) to Schmidt et al. discloses a system that synchronizes the sensor data from a number of underwater vehicles by placing a synchronization subsystem in each underwater vehicle. The synchronization subsystem synchronizes the sensor data by periodically resynchronizing its clock with other synchronization subsystems' clocks. Since the minimum time interval required between resynchronization depends on the accuracy and stability of the clock in the synchronization subsystem, the synchronization subsystem typically includes a highly accurate clock to timestamp each sensor-data sample. Accurate clock synchronization is achieved by frequent optical or acoustic communication among the vehicles. Sensor data may be processed in each vehicle in real time or near real time, or they may be stored in a data unit and processed later, when the vehicle is docked at a network node or when the vehicle is recovered. Each vehicle requires an accurate clock in the synchronization subsystem and a wireless (optical or acoustic in this case) communication system for resynchronization of the clocks during data collection. Furthermore, the wireless communication system consumes additional electrical power for clock resynchronization. If the system is used for small battery-powered sensing devices, the use of a wireless communication system in each device increases the size and cost of the device because of the additional electrical components needed for the wireless communication system, and because of the extra energy drained from the battery, necessitating a larger battery.

U.S. Pat. No. 5,566,180 (1996) and U.S. Pat. No. 6,654,356 B1 (2003), all to Eidson et al., disclose a method for synchronization and syntonization of local clocks of two nodes in a data-communication network by having the nodes send local-time information to each other using the data-communication network, and then having each node compare the difference between the received local-time information and its own local-time information. When the purpose of the nodes is to perform control or sensing function, the synchronization method requires an accurate local clock in each node and a data-communication network for frequent synchronization and syntonization of the local clocks. The synchronization system is not suitable for small portable devices, because a wired data communication network would restrain the portability of the devices and a wireless data-communication network would increase the size, power consumption, and cost of the devices.

The need for time synchronization of sensor data of a battery-powered system is exemplified in a physical-activity monitoring system described by K. Zhang et al. in "Measurement of Human Daily Physical Activity", Obesity Research, Vol. 11, No. 1, 2003, pages 33-40. The system uses five small sensors attached to the body of a human subject to monitor physical activity of the subject, with two sensors placed at the anterior sides of the thighs, two sensors at the inferior sides of the feet, and the fifth sensor below the angle of the sternum. The output electrical signal of each sensor is transmitted through a cable to a data-collection device worn at the waist, so that types of physical activity can be identified from the synchronous signals from all of the sensors on the body. For future work, the authors of the paper propose wireless transmission of the sensor signals during data collection to a data-collection device to alleviate the inconvenience of wearing multiple wired sensors. However, as discussed above, incorporating a wireless communication system in each sensor increases the size and cost of the sensor.

L. Bao and S. S. Intille describe a wireless physical-activity monitoring system in "Activity Recognition from User-Annotated Acceleration Data", Proceedings of the Second International Conference on Pervasive Computing 2004, pages 1-17. In the system, accelerometers are placed on each human subject's right hip, dominant wrist, non-dominant upper arm, dominant ankle, and non-dominant thigh to recognize ambulation, posture, and other physical activities. During a data-collection session, data of the accelerometer at each location are timestamped with an independent quartz-crystal clock and stored locally, so that after data collection the accelerometer data from all the different locations can be processed together to identify the types of physical activity performed. To achieve synchronization of the data samples obtained with independent clocks without using wired or wireless communication links, all the accelerometers are shaken together simultaneously with a fixed sinusoidal pattern at the beginning and end of each data-collection session. Then, during data processing, the authors use a computer to visually align the peaks of these distinct beginning and end sinusoidal signal patterns among all the accelerometers. Finally, timestamps of acceleration data are linearly scaled between the manually aligned start and end points. The post data-collection synchronization technique described in this paper is not practical for widespread use, because it requires sinusoidal vibration of the accelerometers before and after each data-collection session and tedious manual alignment of the accelerometer data. For future research, the authors of this paper recommend using small wireless accelerometers and a mobile computer to receive the wireless accelerometer data.

Physical activity, as a major form of energy expenditure, is considered one of the most important factors in the etiology, prevention, and treatment of obesity, and the development of an accurate physical-activity monitoring system to estimate energy expenditure for both research and widespread use has become a pressing need. The pedometer, a conventional device for counting the number of physical steps a user takes, fails to monitor other types of physical activity, and alternative accelerometer-based devices that monitor more types of physical activity are often inconvenient or expensive—significant barriers for integration into mainstream society. Because simultaneous data from multiple sensors on different parts of the subject's body are required for identifying the types of physical activity performed, using a wireless communication port in each sensor to transmit data during data collection has been proposed by many leading researchers in the field as a way to overcome the inconvenience of wearing multiple wired sensors. However, this approach suffers from a number of disadvantages:

(a) A wireless data recorder worn by the subject or installed in a mobile computer nearby is needed to receive the simultaneous sensor data.

(b) The limited number of wireless signal channels available for public use can result in signal interference if users in close proximity wear similar devices.

(c) Intermittent signal loss may occur when metal objects in the vicinity absorb transmitted electromagnetic signals, or when an antenna orientation changes while a physical activity is being performed.

(d) The transmitted radio-frequency signals can be tracked and decoded by undesired third parties, compromising the privacy of the user.

(e) The required transmission power for wireless communication during data collection drains extra energy from the battery, necessitating a larger battery.

(f) The wireless components, such as external inductors and an antenna, increase the size of the sensor.

(g) The manufacturing cost is increased because of the wireless component cost and labor cost for testing and tuning the wireless communication ports.

The use of post data-collection synchronization instead of wireless communication during data collection for a physical-activity monitoring system retains the benefit of user convenience while avoiding the disadvantages of wireless communication discussed above. However, this approach has been unviable in the past because of the impracticality of existing techniques to compensate for the time drift of the independent quartz-crystal local clock located in each sensor unit. The accuracy of common low-cost surface-mounted quartz crystals is 0.002 to 0.010%, resulting in a time drift of 1.7 to 8.6 seconds a day. Previous attempts to synchronize accelerometer data have required shaking all the accelerometers of a multi-accelerometer system simultaneously with a fixed sinusoidal pattern before and after a data-collection session.

SUMMARY

In accordance with a first embodiment of the post data-collection synchronization system comprising at least one sensor unit and a data processor, each sensor unit has a local clock, and the data processor has a reference local clock. The data processor reads and stores its reference local-clock times and each sensor unit's local-clock times before and after a data-collection session, and then the data processor computes a time-scaling factor for converting each sensor unit's local-clock data-sampling times to their corresponding reference local-clock data-sampling times. The data processor uses a data-interpolation technique to interpolate sensor data to approximate simultaneous sensor-data values at the desired reference local-clock times. In some cases, the approximation may be exact. When only one sensor unit is used in the system, the system can synchronize the sensor unit's local-clock timestamped data with the data processor's reference local clock.

In accordance with a second embodiment of the post data-collection synchronization system comprising a plurality of sensor units and a data processor, each sensor unit has a local clock, and the data processor has a local clock. The data processor communicates with each sensor unit to read and to store the sensor unit's local-clock times before and after a data-collection session, and the data processor uses its local clock to estimate the time delays of the communication. Using the local-clock times of a sensor unit as the reference local-clock times, the data processor computes a time-scaling factor for converting each sensor unit's local-clock data-sampling times to their corresponding reference local-clock data-sampling times. The data processor then uses a data-interpolation technique to interpolate sensor data to approximate simultaneous sensor-data values at the desired reference local-clock times. In some cases, the approximation may be exact.

In accordance with a third embodiment of the post data-collection synchronization system comprising a synchronization-signal transmitter, a data processor, and a plurality of sensor units, each sensor unit has a local clock. The synchronization-signal transmitter transmits a synchronization signal to all of the sensor units simultaneously before and after a data-collection session, so that the initial and final local-clock times are stored locally in the sensor units simultaneously and are sent to the data processor after the data-collection session. Using the local-clock times of any one of the sensor units as the reference local-clock times, the data processor computes a time-scaling factor for converting each sensor unit's local-clock data-sampling times to their corresponding reference local-clock data-sampling times. The data processor then uses a data-interpolation technique to interpolate sensor data to approximate simultaneous sensor-data values at the desired reference local-clock times. In some cases, the approximation may be exact.

DRAWINGS

Figures

DETAILED DISCRIPTION

FIGS. 1, 2, 3, and 4—First Embodiment

A first embodiment of the post data-collection synchronization system is illustrated in FIGS. 1, 2, 3, and 4. The synchronization system provides approximations of simultaneous sensor data from multiple sensor units located at different physical locations, without the need for wired or wireless communication to transmit the data during a data-collection session. During data-collection, the sensor data are stored in each sensor unit locally, and after data collection they are sent to a data processor for time synchronization with the data processor's local clock, which serves as the reference local clock. When only one sensor unit is used in the system, the system can synchronize the sensor unit's local-clock timestamped data with the data processor's reference local clock.

Figure 1:
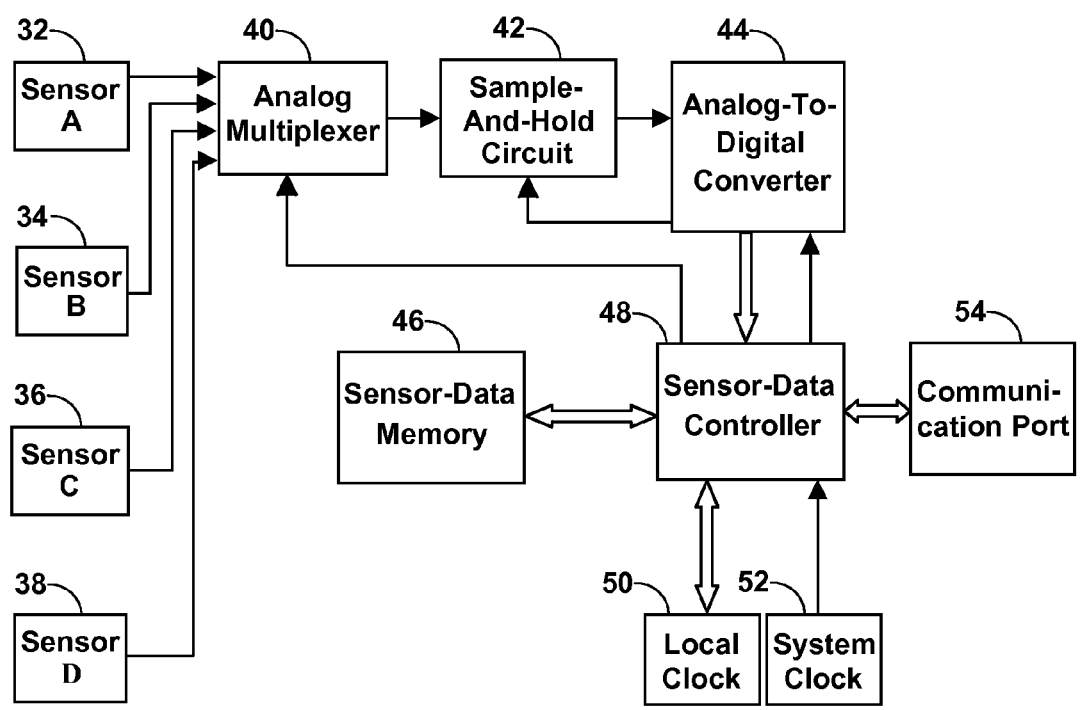
FIG. 1 is a block diagram showing schematically a sensor unit in accordance with the first embodiment.
Figure 2:
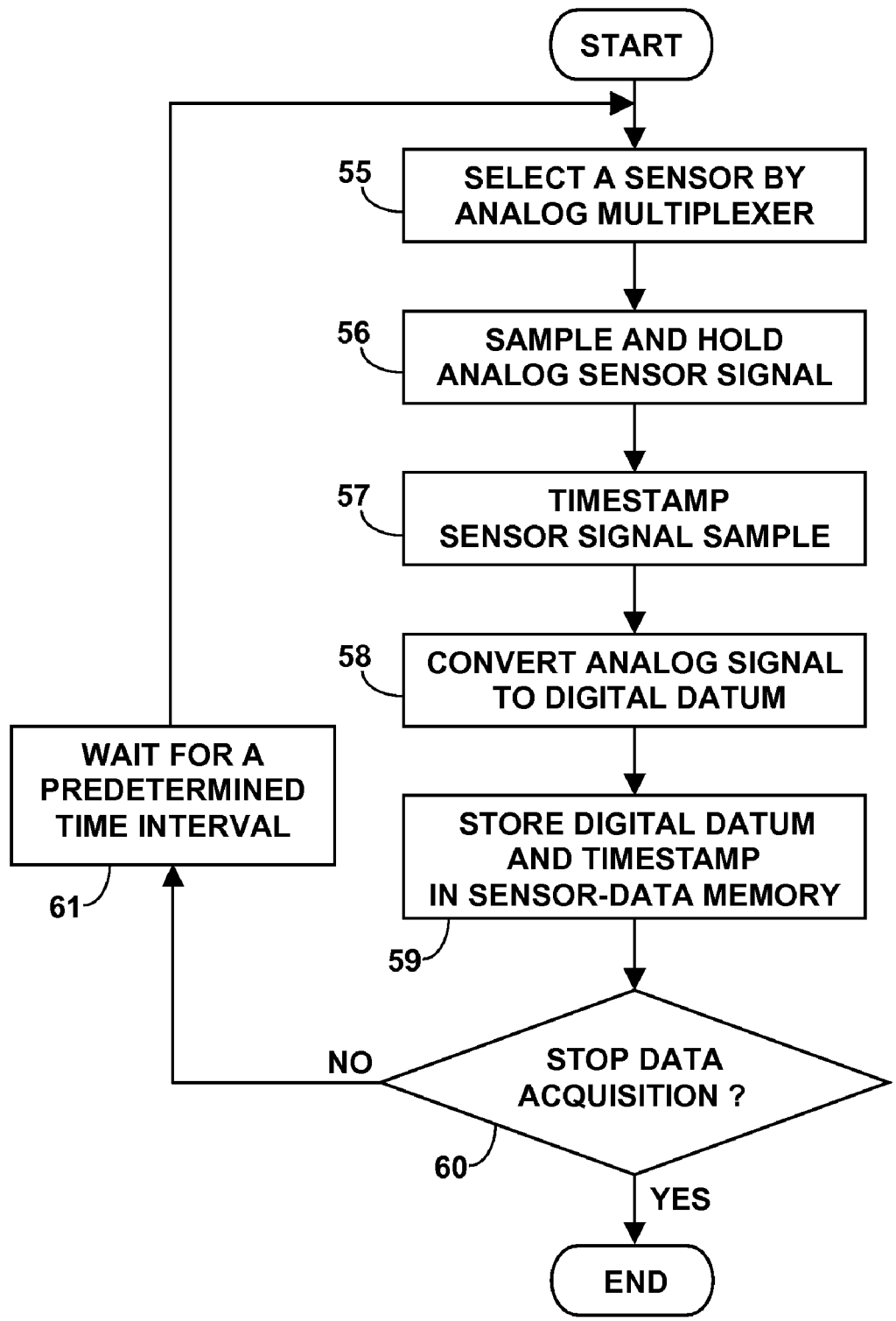
FIG. 2 is a flow diagram illustrating the operation of a sensor-data controller in the sensor unit in accordance with the first embodiment.

FIG. 1 is a block diagram showing schematically a sensor unit. In the sensor unit, the analog signal from each of four sensors 32, 34, 36, 38 (Sensor A, Sensor B, Sensor C, Sensor D, respectively) is selected by an analog multiplexer 40 at predetermined time intervals, under the control of a sensor-data controller 48, which uses a local clock 50 to timestamp the sampled data. A system clock 52 in the sensor unit provides the operation timing for sensor-data controller 48, which is usually a microprocessor. In some applications, local clock 50 also serves as the system clock, so that system clock 52 is not needed. Sensor A, Sensor B, Sensor C, and Sensor D can be temperature sensors, voltage sensors, light sensors, heart-rate sensors, accelerometers, video sensors, microphones, or other types of sensors, and they can be the same type of sensor or a combination of different types of sensors. The data-sampling rates of sensors 32, 34, 36, 38 can be the same or different. The flow diagram for the operation of sensor-data controller 48 is presented in FIG. 2. In FIG. 2, after a sensor is selected at step 55 by analog multiplexer 40, which is under the control of sensor-data controller 48, sensor-data controller 48 activates an analog-to-digital converter 44, which uses a sample-and-hold circuit 42 (FIG. 1) to sample and hold the analog sensor signal at step 56. Sensor-data controller 48 timestamps the signal sample with the local-clock time at step 57. Analog-to-digital converter 44 converts the analog signal sample to the corresponding digital datum at step 58 and sends the digital datum to sensor-data controller 48, which stores the digital datum along with its timestamp in a sensor-data memory 46 (FIG. 1) at step 59. If the user does not stop the data acquisition at step 60, sensor-data controller 48 waits until a predetermined local-clock time interval or predetermined system-clock time interval has elapsed at step 61 before it selects the same or a different sensor for data acquisition by analog multiplexer 40 at step 55. If the digital data are obtained by sampling each sensor's signal at a predetermined regular local-clock time interval, and each sensor's data are stored in sensor-data memory 46 in sequential order, the local-clock sampling time of each data sample in sensor-data memory 46 can be determined from its location in sensor-data memory 46, provided that at least one of the stored data is timestamped with local clock 50 (FIG. 1). Communication port 54 in the sensor unit facilitates communication between the sensor unit and the data processor.

Although FIG. 1 shows that the sensor unit contains four sensors, the sensor unit may contain different numbers of sensors in different applications. Sample-and-hold circuit 42 and analog-to-digital converter 44 are not required for sensors that produce digital output data, and analog multiplexer 40 should be replaced with a digital multiplexer in this case. Furthermore, if the sensor unit contains only one sensor, the analog or digital multiplexer is not needed.

Figure 3:
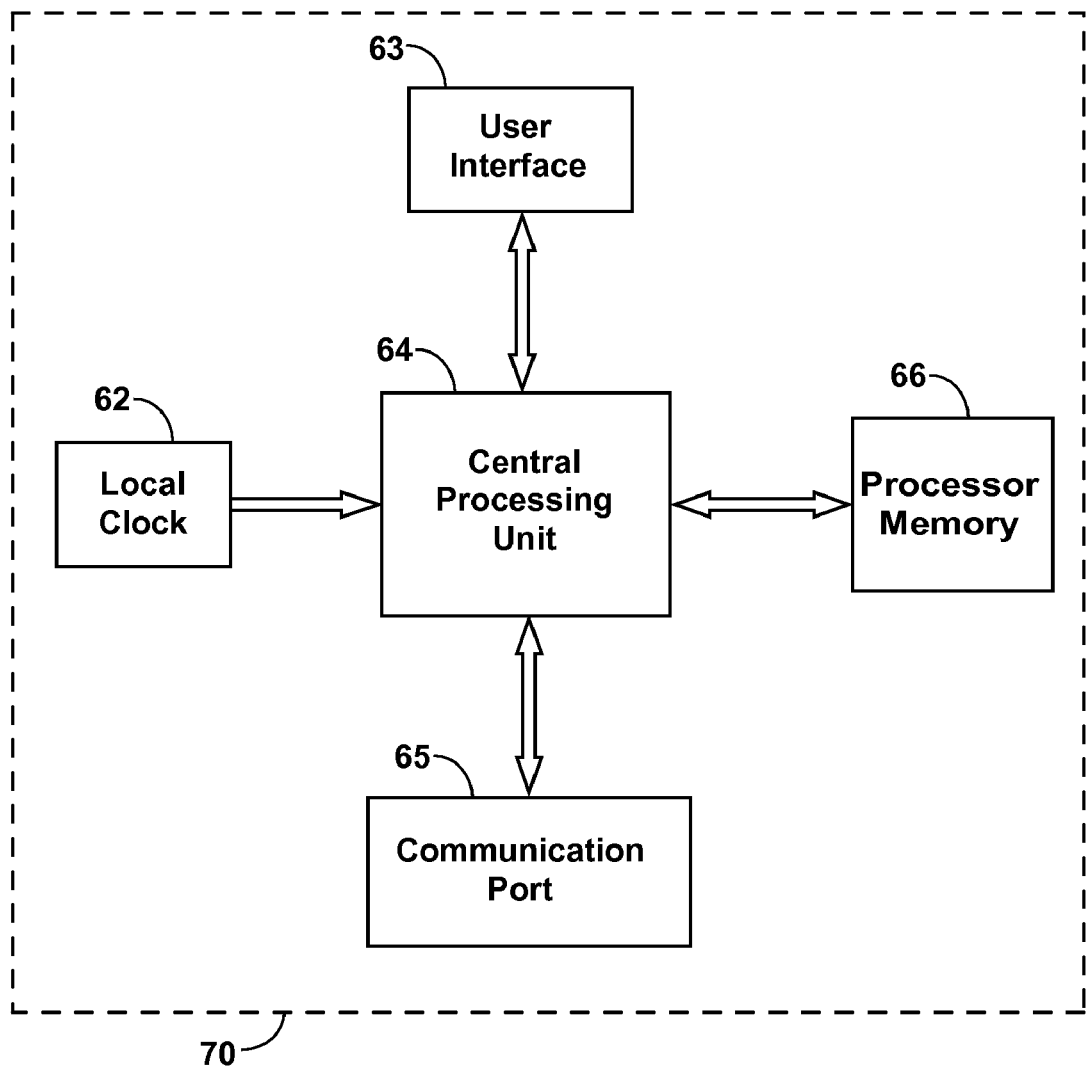
FIG. 3 is a block diagram showing schematically the data processor in accordance with the first embodiment.

FIG. 3 is a block diagram of a data processor 70. Data processor 70 includes a central processing unit 64 for data processing, a local clock 62, a processor memory 66 for storing data and local-clock times, a communication port 65 for communicating with the sensor units, and a user interface 63, such as a keyboard and a monitor, for providing communication with the user. Processor memory 66 can be random-access memory (RAM), flash memory, hard disk, or any type of digital memory. Central processing unit 64 can be configured to perform mathematical computation, data interpolation, storing and retrieving data, and reading and sending data through communication port 65, etc., as well known in the art.

Figure 4:
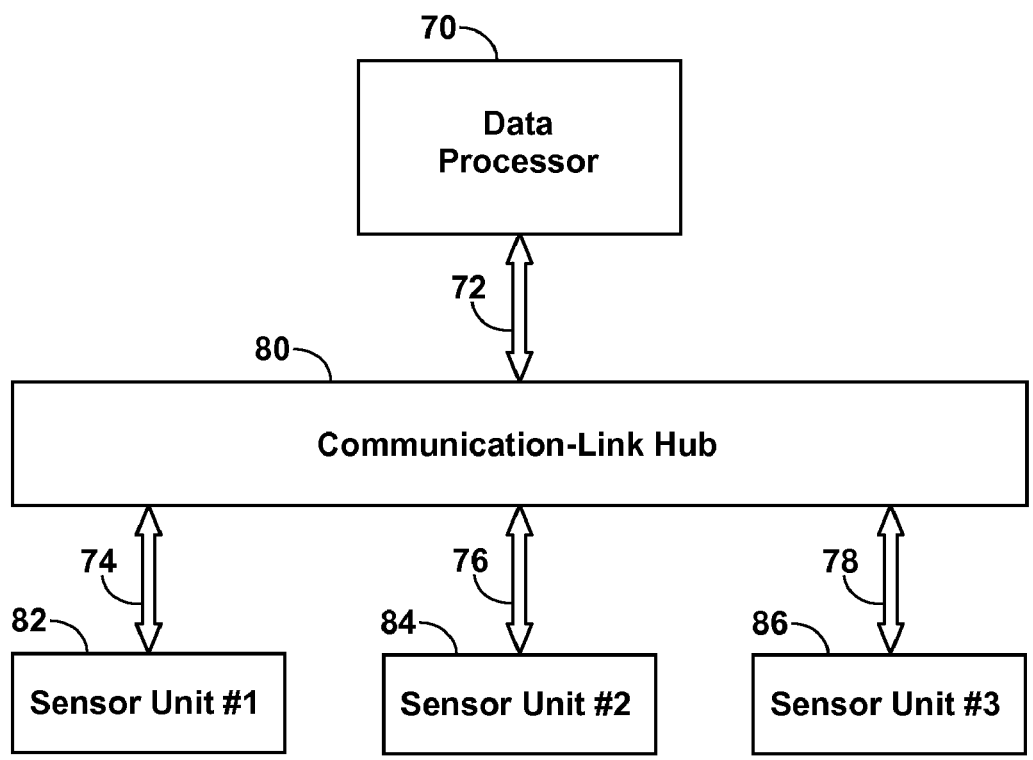
FIG. 4 is a block diagram illustrating schematically a communication-link hub providing communication between the data processor and each of three sensor units in accordance with the first embodiment.

FIG. 4 illustrates the communications between each sensor unit 82, 84, 86 and data processor 70 through communication means, such as communication links 72, 74, 76, 78 and a communication-link hub 80, which provide wired or wireless serial or parallel data communications. Data processor 70 uses communication link 72 to communicate with communication-link hub 80, which in turn uses the communication links 74, 76, 78 to communicate with sensor units 82, 84, 86, respectively. Examples of communication-link hubs are RS-232 serial hubs and wired or wireless Universal-Serial-Bus (USB) hubs, which are commonly used for personal computers to communicate with a plurality of computer-peripheral devices. If communication link 72 is a wireless communication link that can facilitate direct communication between data processor 70 and each sensor unit 82, 84, 86 before and after a data-collection session, then communication-link hub 80 is not needed. Communication links 72, 74, 76, 78 may be the same type or different types of communication link, and they may be wired or wireless communication links, such as electrical, optical, acoustic, magnetic, or electromagnetic data links, etc., with corresponding communication ports in data processor 70 and sensor units 82, 84, 86. Using communication-link hub 80, data processor 70 receives each sensor unit's local-clock times and data, and they are stored in processor memory 66 (FIG. 3). Although not illustrated in FIG. 4, communication-link hub 80 can also provide electrical power to charge the batteries of sensor units 82, 84, 86, so that wired or wireless communication using communication port 54 (FIG. 1) before or after a data-collection session does not drain energy from the batteries.

In the first embodiment, the data processor's local clock serves as the reference local clock, so that the local-clock times received from sensor units 82, 84, 86 can be converted to their corresponding reference local-clock times. Data processor 70 uses a data-interpolation technique to interpolate sensor data to approximate simultaneous sensor-data values at the desired reference local-clock times. In some cases, the approximation may be exact. In FIG. 4, a total of three sensor units (Sensor Unit #1, Sensor Unit #2, and Sensor Unit #3) communicate with data processor 70 through communication-link hub 80, although a different number of sensor units may communicate with data processor 70. When only one sensor unit is used in the system, the system can synchronize the sensor unit's local-clock timestamped data with the data processor's reference local clock.

Figure 5:
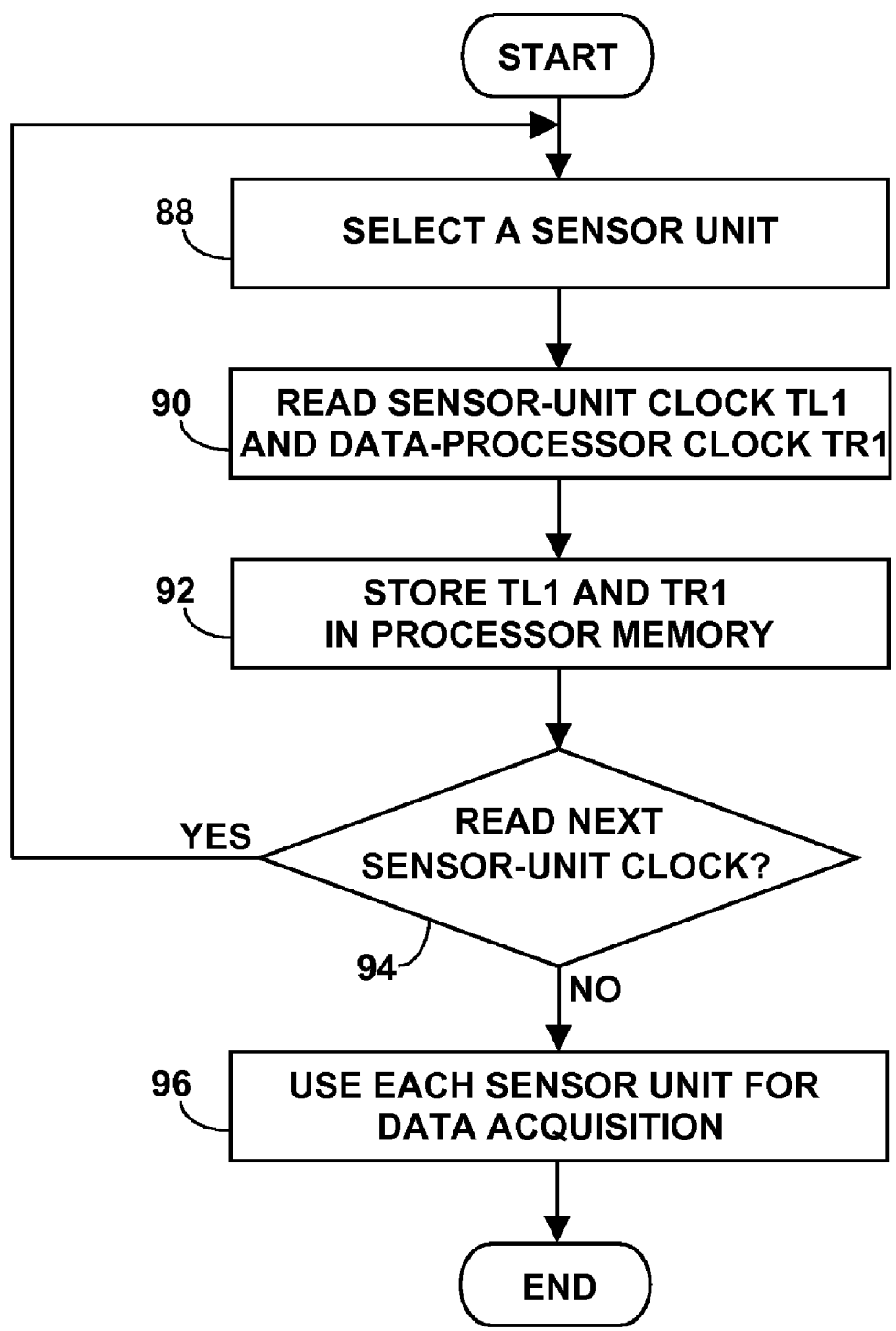
FIG. 5 is a flow diagram illustrating the synchronization operation of the data processor before a data-collection session in accordance with the first embodiment.
Figure 6:
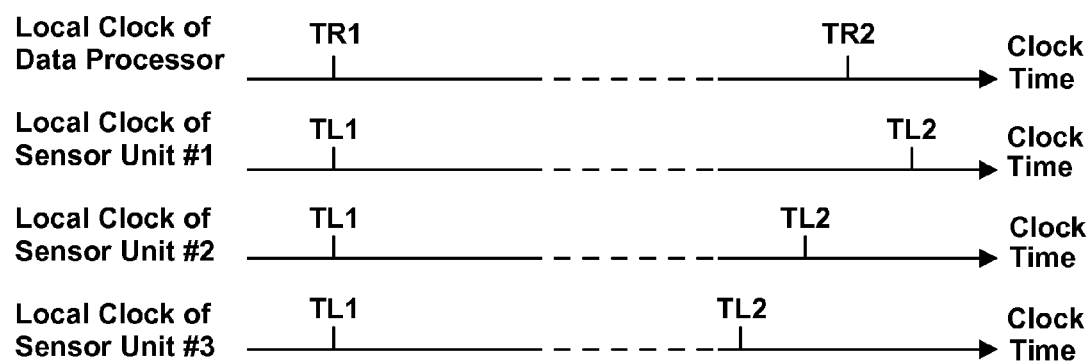
FIG. 6 is a timing diagram illustrating different time drifts of the local clocks in accordance with the first embodiment.
Figure 7:
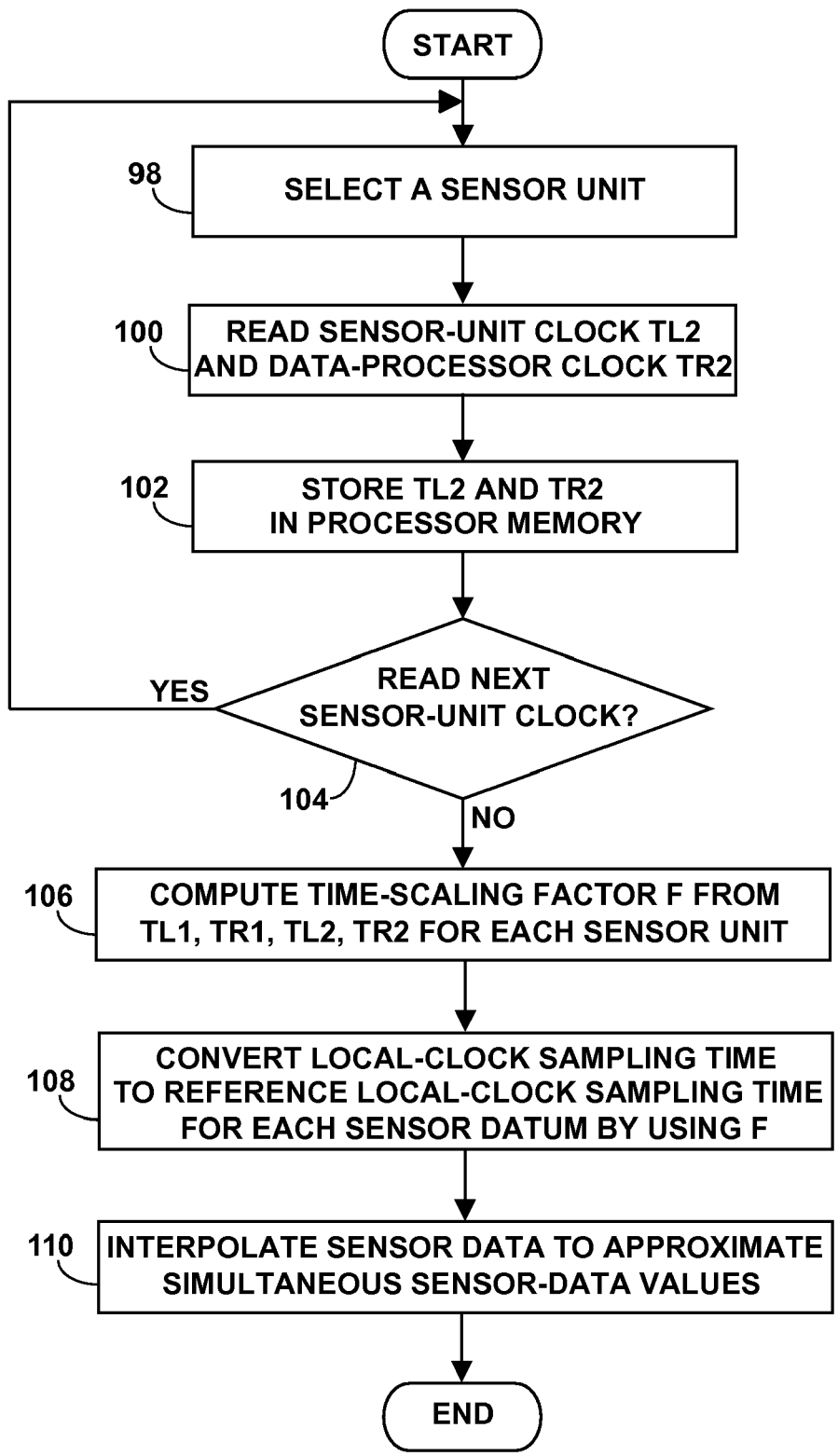
FIG. 7 is a flow diagram illustrating the synchronization operation of the data processor after a data-collection session in accordance with the first embodiment.

Synchronization Operation—FIGS. 5, 6, and 7

A flow diagram for the synchronization operation before a data-collection session is shown in FIG. 5. Before a data-collection session, each sensor unit 82, 84, 86 communicates with data processor 70 through communication-link hub 80 (FIG. 4), and data processor 70 selects a sensor unit at step 88. At step 90, data processor 70 reads the sensor unit's current local-clock time, which is the initial local-clock time TL1, and the data processor's current local-clock time TR1, which is the initial reference local-clock time. Data processor 70 stores TL1 and TR1 in processor memory 66 (FIG. 3) at step 92. At step 94, data processor 70 repeats this process for the next sensor unit, until each sensor unit has been selected. At step 96, each sensor unit is used for data acquisition, and it can be located anywhere physically without communicating with data processor 70 or other sensor units.

FIG. 6 is a timing diagram illustrating different time drifts of the local clocks. In FIG. 6, the local clock of Sensor Unit #1 runs faster than the reference local clock of data processor 70, but the local clock of Sensor Unit #2 runs slower than the reference local clock, and the local clock of Sensor Unit #3 runs even slower.

A flow diagram for the synchronization operation after a data-collection session is shown in FIG. 7. After a data-collection session, each sensor unit 82, 84, 86 resumes communication with data processor 70 through communication-link hub 80 (FIG. 4), and data processor 70 selects a sensor unit at step 98. At step 100, data processor 70 reads the sensor unit's current local-clock time, which is the final local-clock time TL2, and the data processor's local-clock time TR2, which is the final reference local-clock time. At step 102, data processor 70 stores TL2 and TR2 in processor memory 66 (FIG. 3). At step 104, data processor 70 repeats the above processes for the next sensor unit, until each sensor unit has been selected.

At step 106, data processor 70 computes the elapsed time of each sensor unit's local clock, which is the difference between TL2 and TL1, and the elapsed time of the reference local clock, which is the difference between TR2 and TR1. At step 106, data processor 70 also computes a time-scaling factor F, which is the ratio of the difference between the final and initial reference local-clock times and the difference between the final and initial local-clock times, as follows:

$$F = (TR2 - TR1)/(TL2 - TL1)$$

At step 108, data processor 70 uses the time-scaling factor F to convert the local-clock sampling time of each sensor datum to its corresponding reference local-clock sampling time. Because of the time delays through the communication links, including through communication-link hub 80 and the communication ports 54, 65 (FIGS. 1 and 3), the current local-clock time of the sensor unit will have already advanced by the time TL1 or TL2 is received by data processor 70. However, since only the time difference TL2−TL1 is used for computing F, F is an accurate conversion factor if the time delays through the communication links are small relative to TL2−TL1, or if the time delays are nearly constant. Alternatively, if the time delays for receiving TL1 and TL2 through the communication links are known, the current local-clock times can be estimated by adding the corresponding time delays to TL1 and TL2.

When the stored data samples of a sensor unit (sensor unit 82, 84, or 86) are sent to data processor 70 (this process is not shown in FIG. 7), at least one of these data samples has a timestamp from the sensor unit's local clock 50 (FIG. 1). If a regular local-clock time interval TLi is used for data acquisition, the local-clock timestamp TLb of a data sample, usually the first data sample in a data-collection session, can be used to compute the local-clock sampling times of all the data in a sequence of sensor data. Data processor 70 converts the local-clock timestamp TLb to the reference local-clock timestamp TRb as follows:

$$TRb = TR1 + (TLb - TL1) \times F$$

In the above equation, the local-clock time difference TLb−TL1 is multiplied by the time-scaling factor F to convert it to the reference local-clock time difference.

TLi is also converted to the reference local-clock time interval by multiplying TLi with the time-scaling factor F, so that the reference local-clock sampling time TRs for each datum can be obtained as follows:

$$TRs = TRb + TLi \times F \times N$$

where N is the number of sampling intervals away from the reference local-clock timestamp TRb, and N is zero for the datum with timestamp TRb. N is a positive integer for data sampled after TRb, and it is a negative integer for data sampled before TRb.

In FIG. 1, the sensor unit contains more than one sensor, and the reference local-clock sampling time TRs for any data sample can be obtained as discussed above. In many applications, the data-sampling times for different sensors in the sensor unit maintain fixed time differences among each other, and these local-clock time differences can be multiplied by the time-scaling factor F to convert them to their corresponding reference local-clock time differences. Once the reference local-clock sampling times for a sensor's data are obtained, the reference local-clock sampling times for another sensor's data can be computed by using the fixed reference local-clock time difference.

If a regular system-clock time interval (as shown in FIG. 1, system clock 52 in the sensor unit provides the operation timing for sensor-data controller 48) instead of a regular local-clock time interval is used for the data sampling, each data sample can be timestamped with local clock 50 (FIG. 1). Data processor 70 can convert each local-clock timestamp TLb to the reference local-clock timestamp TRb as shown above. Alternatively, the local-clock timestamps of two data samples, usually the data samples at the beginning and end of a data-collection session, can be used by data processor 70 for computing the local-clock sampling times of all the data samples by linear time interpolation and extrapolation of the local-clock timestamps, and the local-clock sampling times can be converted to the reference local-clock sampling times as discussed above.

After data processor 70 converts the local-clock sampling times of the sensor units' data to the reference local-clock sampling times at step 108, data processor 70 uses a data-interpolation technique, such as low-pass filtering with a finite-impulse-response (FIR) filter or linear interpolation between consecutive data samples, to interpolate sensor data to approximate simultaneous sensor-data values at the desired reference local-clock times at step 110. In some cases, such as low-pass filtering of a band-limited signal, the approximation may be exact.

In the first embodiment, approximations of simultaneous sensor data from multiple sensor units are achieved without the need for setting each sensor unit's local-clock time equal to the data processor's reference local-clock time, because only the time differences of the local clocks are used by data processor 70 for time scaling in the synchronization operation. Local clock 62 (the reference local clock) of data processor 70 is usually a real-time clock, such as that used in a personal computer, to indicate the date and time of day. In fact, a personal computer can be used to implement the functions of data processor 70. To facilitate computation, the reference local-clock time can be converted to the number of seconds or milliseconds (or even microseconds for a high-resolution real-time clock) elapsed from a predetermined date and time, such as midnight on Dec. 31, 2007. Alternatively, reference local clock 62 in data processor 70 can be a low-cost quartz-crystal oscillator and a simple digital binary counter to count the number of elapsed clock cycles, with no association with a real-world clock.

Local clock 50 (FIG. 1) of each sensor unit 82, 84, 86 is usually a low-cost quartz-crystal oscillator and a simple digital binary counter to count the number of elapsed clock cycles. Although only the time difference of each sensor unit's local clock is used for post data-collection time scaling and interpolation, the interpolation errors are reduced when the time differences among the sensor units' local clocks are minimized during a data-collection session. If the sensor units' local clocks are running at about the same clock frequency, synchronizing the local clocks just before the beginning of a data-collection session reduces the time differences. This clock synchronization can be achieved by resetting the counters of all the sensor units' local clocks to zero or a predetermined value simultaneously, and data processor 70 or communication-link hub 80 can issue the reset signal. For example, data processor 70 can send a reset signal through communication-link hub 80 and communication links 72, 74, 76, 78 to sensor units 82, 84, 86 for resetting the counters of the local clocks simultaneously to a predetermined value, such as zero, at the beginning of a data-collection session. This reset signal may be electrical, magnetic, electromagnetic, optical, acoustic, or mechanical, etc., with a corresponding signal receiver incorporated in communication port 54 of each sensor unit.

When the local clock of a sensor unit also provides timekeeping function for the user, such as serving as a wristwatch, it may be desirable to set the local-clock time of each sensor unit 82, 84, 86 equal to the reference local-clock time of data processor 70 before a data-collection session. In this case, after compensation for the time delays of communication links 72, 74, 76, 78, data processor 70 can send its reference local-clock time (in seconds or milliseconds) to each sensor unit 82, 84, 86 through communication-link hub 80, so that the counters of the local clocks are set to the reference local-clock time (in milliseconds, for example) at the beginning of a data-collection session. Alternatively, the synchronization operation can be performed as follows. Before a data-collection session, data processor 70 sends its current reference local-clock time to each sensor unit 82, 84, 86 to set the sensor unit's local clock time equal to the reference local-clock time, and then data processor 70 reads back the sensor unit's updated local-clock time TL1. Upon reception of TL1, data processor 70 reads its most current reference local-clock time TR1 and stores TL1 and TR1 in processor memory 66 (FIG. 3) as the initial local-clock time and the initial reference local-clock time, respectively, for the elapsed time calculation. After the data-collection session, data processor 70 reads the current local-clock time TL2 from each sensor unit. Upon reception of TL2, data processor 70 reads its most current reference local-clock time TR2 and stores TL2 and TR2 in processor memory 66 as the final local-clock time and the final reference local-clock time, respectively, for the elapsed time calculation. Data processor 70 performs this process for each sensor unit 82, 84, 86, and a time-scaling factor F is computed as (TR2−TR1)/(TL2−TL1) for each sensor unit 82, 84, 86. Unless the time delays through the communication links, including through communication-link hub 80 and communication ports 54, 65 (FIGS. 1 and 3), are known and compensated for, the initial clock readings TL1 and TR1 will be slightly different even after data processor 70 sets the local-clock time of each sensor unit 82, 84, 86 equal to its reference local-clock time. Since only the time differences TL2−TL1 and TR2−TR1 are used for computing F, F is an accurate time-scaling factor if the time delays through the communication links are relatively small or nearly constant. The process of time scaling and interpolation are performed as discussed above.

Figure 8:
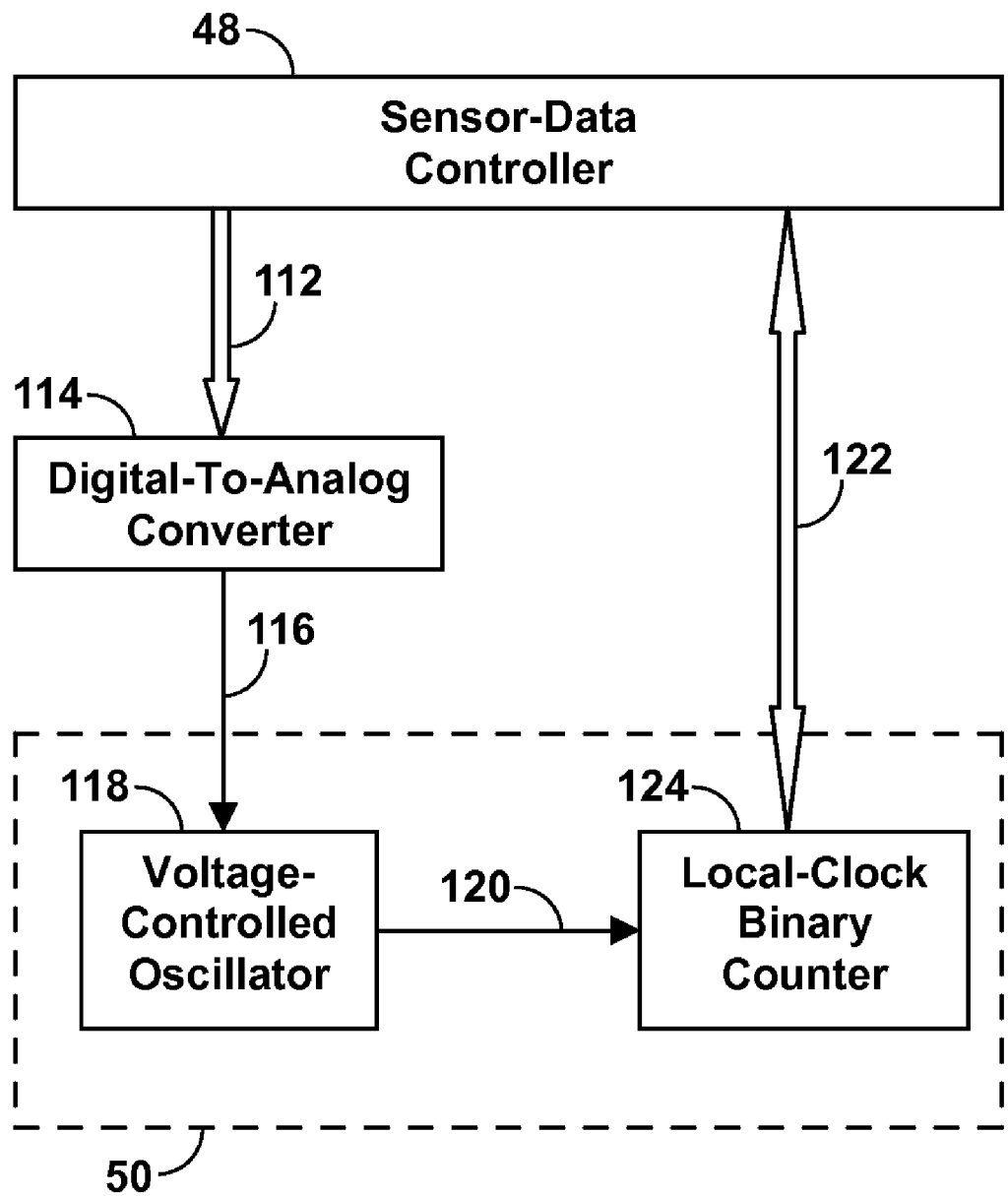
FIG. 8 is a partial block diagram showing schematically the communication between the local clock and the sensor-data controller of a sensor unit, including a means for adjusting the local-clock frequency, in accordance with the first embodiment.

Syntonization Operation—FIG. 8

After a long period of data collection, the time drifts among the sensor units' local clocks may become very large at the end of a data-collection session, even though the local clocks are synchronized at the beginning of a data-collection session. In this case, adjusting each sensor unit's local-clock frequency to match the data processor's reference local-clock frequency more closely reduces the interpolation errors. FIG. 8 is a partial block diagram illustrating a sensor unit's local clock 50 that comprises a voltage-controlled oscillator 118 to facilitate adjustment of the local-clock frequency by sensor-data controller 48. Sensor-data controller 48 uses a local-clock data bus 122 to read and to set the local-clock time. Voltage-controlled oscillator 118, such as a voltage-controlled crystal oscillator, provides a clock signal 120 for a local-clock binary counter 124. In a clock-calibration session, which is similar to a data-collection session, data processor 70 calibrates the local-clock frequency of a sensor unit (sensor unit 82, 84, or 86) by using the elapsed time of the data processor's reference local clock (TR2−TR1) and the elapsed time of the sensor unit's local clock (TL2−TL1) to compute a time-scaling factor F, which is also the frequency ratio of the two clocks, as shown below:

$$F = \text{Freq}R/\text{Freq}L = (TR2-TR1)/(TL2-TL1)$$

where FreqL is the sensor unit's local-clock frequency, and FreqR is the data processor's reference local-clock frequency. During a clock-calibration session, the sensor unit does not need to collect any data, but the session should be long enough to observe a significant difference between the elapsed reference local-clock time TR2–TR1 and the elapsed local-clock time TL2–TL1. The frequency difference between the two clocks, D, can be computed as follows:

$$D = \text{Freq}L - \text{Freq}R = (\text{Freq}R/F) - \text{Freq}R = \text{Freq}R \times (1/F - 1)$$

Using the reference local-clock frequency FreqR as the reference, the local-clock frequency drift D of the sensor unit can be computed from the above equation. Data processor 70 can send frequency-adjustment data (based on the characteristics of voltage-controlled oscillator 118) to sensor-data controller 48 through communication-link hub 80 (FIG. 4). Sensor-data controller 48 sends the frequency-adjustment data through data bus 112 to a digital-to-analog converter 114, which converts the frequency-adjustment data to a control-voltage signal 116 to adjust the frequency of voltage-controlled oscillator 118, so that the frequency of local clock 50 matches that of the reference local clock more closely. Alternatively, control-voltage signal 116 can be adjusted with a potentiometer, and data processor 70 can provide clock-frequency adjustment instructions through user interface 63 (FIG. 3), so that the user can adjust the frequency of local clock 50 manually to match that of the reference local clock 62 more closely.

In certain applications, highly precise adjustment of the local-clock frequency with voltage-controlled oscillator 118 is not required to achieve an acceptable level of interpolation error, and the frequency adjustment can be achieved digitally instead. Although not illustrated in FIG. 8, sensor-data controller 48 in this case can use the digital frequency-adjustment data to change the preset value of the local clock's binary counter 124 to adjust the binary counter's output local-clock frequency, so that the output local-clock frequency matches the reference local-clock frequency more closely.

FIGS. 9, 10, 11, and 12—Second Embodiment

A second embodiment of the post data-collection synchronization system is illustrated in FIGS. 9, 10, 11, and 12. The second embodiment is similar to the first embodiment, except that a sensor unit's local clock, instead of the data processor's local clock, serves as the reference local clock for the post data-collection synchronization. This happens, for example, in a physical-activity monitoring system in which the local clock of a sensor unit is also a wristwatch. In this case, the wristwatch provides time-keeping function for the user in addition to serving as the reference local clock of the synchronization system. In the second embodiment, the data processor's local clock is not required for the post data-collection synchronization, but it can be used for estimating the time delays of the communication links between the data processor and each sensor unit. Although the second embodiment can be used in many applications, it is illustrated by a physical-activity monitoring system with three sensor units in the following.

Figure 9:
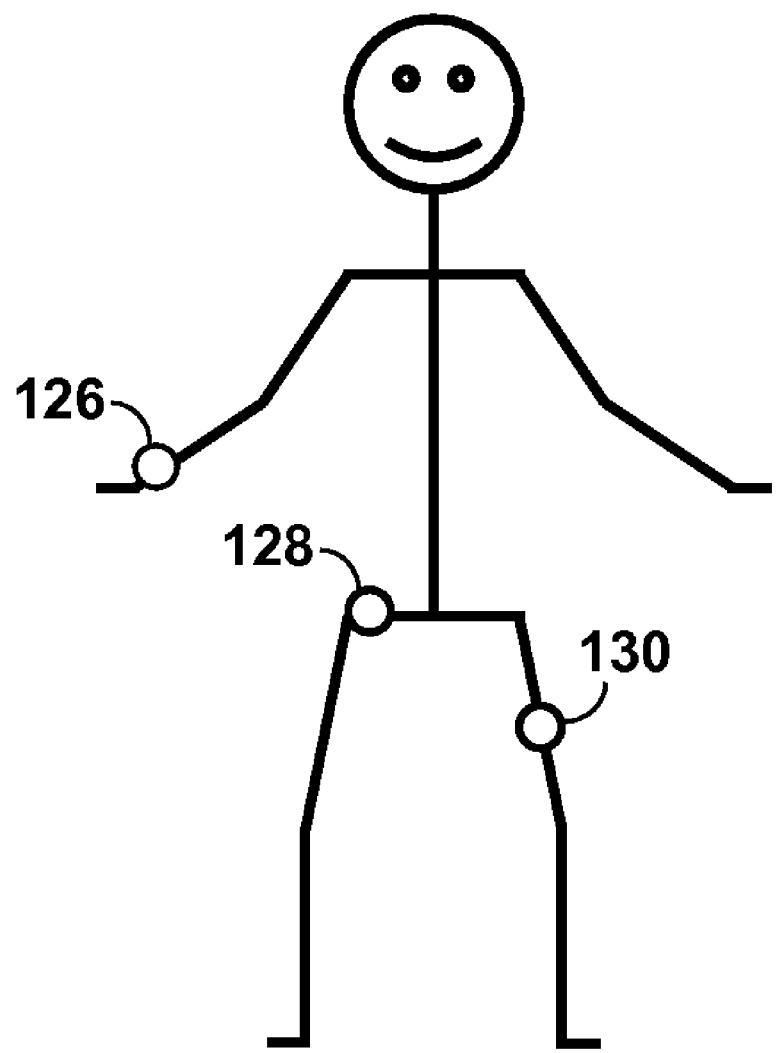
FIG. 9 is a graphical illustration of possible locations of three sensor units for monitoring physical activity of a human being in accordance with the second embodiment.
Figure 10:
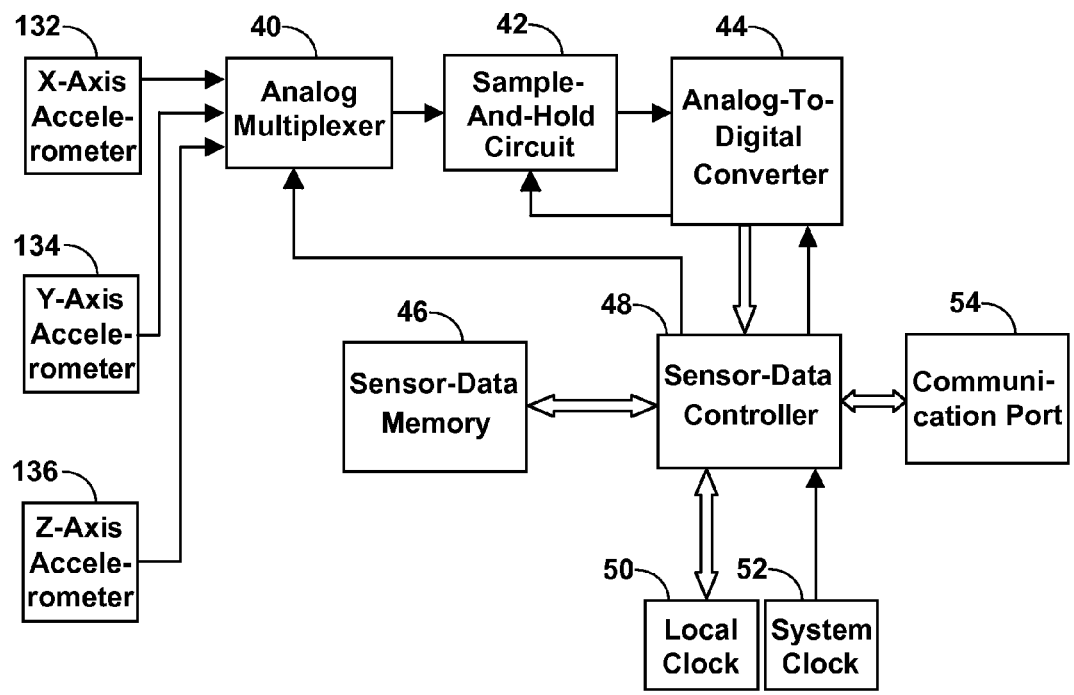
FIG. 10 is a block diagram showing schematically a sensor unit in accordance with the second embodiment.

FIG. 9 illustrates three sensor units of a physical-activity monitoring system located on the body of a human being. In this physical-activity monitoring system, wrist sensor unit 126 is placed on the wrist of the dominant hand, waist sensor unit 128 is placed on the waist on the same side of the body, and thigh sensor unit 130 is placed on the thigh on the opposite side of the body. In the second embodiment, the accelerometers in sensor units 126, 128, 130 are used to monitor the orientations and movements of the body segments of the human being to detect the types and intensities of physical activity performed, and the synchronization system is employed to provide approximations of simultaneous accelerometer data of sensor units 126, 128, 130. The accelerometers in sensor units 128, 130 on the waist and the thigh, respectively, can detect relatively stationary activities, such as standing, sitting, or lying down, from the orientation of the waist and the thigh with respect to the vertical direction of gravitational acceleration. Likewise, sensor units 128, 130 on the waist and the thigh, respectively, can detect more rigorous activities, such as walking, running, or jumping, from simultaneous, fast-changing accelerations. In addition, the accelerometers in wrist sensor unit 126 placed on the dominant wrist are useful in discriminating daily activities involving the upper extremities. FIG. 10 is a block diagram of a sensor unit (sensor unit 126, 128, or 130), which is similar to the block diagram of the sensor unit of the first embodiment (FIG. 1), and the operations of both sensor units are the same. In each sensor unit 126, 128, 130 of the second embodiment, the sensors are three accelerometers 132, 134, 136 for measuring acceleration of a body segment in three orthogonal directions, X, Y, and Z, respectively. Although three accelerometers are illustrated in FIG. 10, a different number of accelerometers can be used for detecting the motion of a particular body segment. In the second embodiment, local clock 50 of wrist sensor unit 126 is also a wristwatch, and provides time-keeping function for the user in addition to serving as the reference local clock of the synchronization system.

Figure 11:
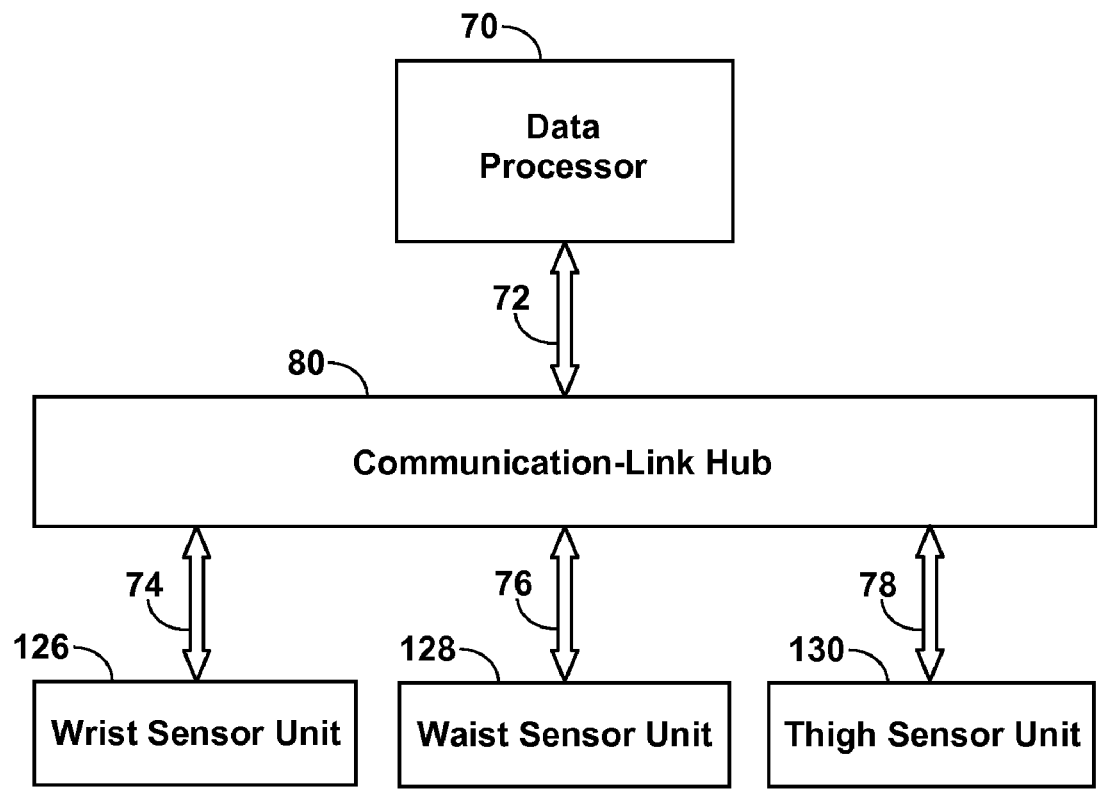
FIG. 11 is a block diagram illustrating schematically a communication-link hub providing communication between the data processor and each of three sensor units, in accordance with the second embodiment.

FIG. 11 illustrates schematically the communication between data processor 70 and each sensor unit 126, 128, 130 through communication-link hub 80. The block diagram of data processor 70 of the second embodiment is the same as that of the first embodiment (FIG. 3). In the second embodiment, data processor 70 uses its local clock 62 to estimate the time delays through the communication links, including through communication-link hub 80 and communication ports 54, 65 (FIGS. 3 and 10). Before and after a data-collection session, data processor 70 uses communication link 72 to communicate with communication-link hub 80, which in turn uses communication links 74, 76, 78 to communicate with sensor units 126, 128, 130, respectively. If communication link 72 is a wireless communication link that can facilitate direct communication between data processor 70 and each sensor unit 126, 128, 130 before and after a data-collection session, then communication-link hub 80 is not needed. Communication links 72, 74, 76, 78 may be the same type or different types of communication link, and they may be wired or wireless communication links, such as electrical, optical, acoustic, magnetic, or electromagnetic data links, etc., with corresponding communication ports in data processor 70 and sensor units 126, 128, 130. Although not shown in FIG. 11, communication-link hub 80 can also provide electrical power to charge the batteries in sensor units 126, 128, 130, so that wired or wireless communication using communication port 54 (FIG. 10) before or after a data-collection session does not drain energy from the batteries.

During a data-collection session, no wired or wireless communication among sensor units 126, 128, 130 and data processor 70 is required. By eliminating wired or wireless communication during data collection, the privacy of the human being is protected, and the human being does not need to wear an additional central data-collection unit to receive wired or wireless signals from the sensor units. Furthermore, by circumventing data transmission during a data-collection session, the power requirement of sensor units 126, 128, 130 is reduced, allowing battery size to be smaller. This embodiment successfully addresses the problems exhibited by current state of the art physical-activity monitoring systems.

Figure 12:
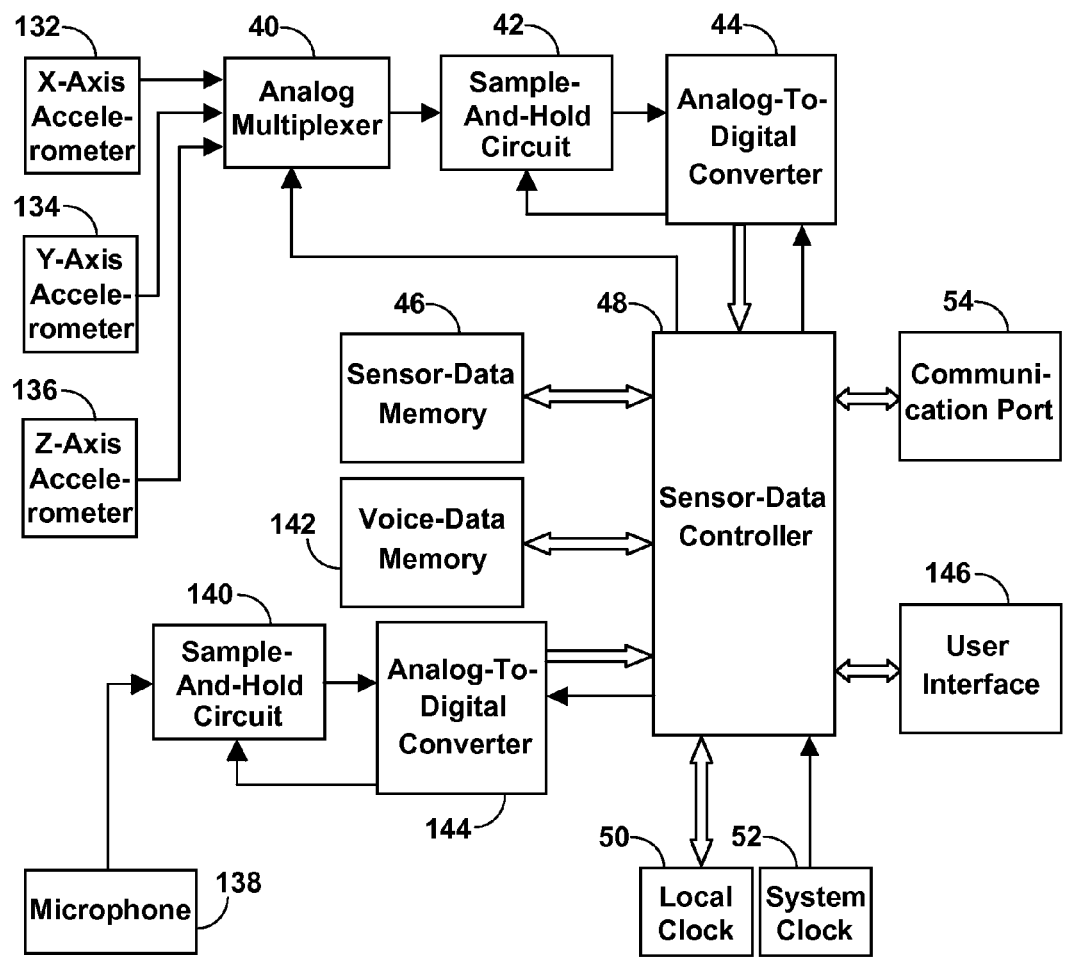
FIG. 12 is a block diagram showing schematically a wrist sensor unit that incorporates a microphone for the user to verbally record types of physical activity performed, in accordance with the second embodiment.

Although only three sensor units (sensor units 126, 128, 130) are shown in FIG. 11, a different number of sensor units may be used in the second embodiment. Furthermore, each sensor unit 126, 128, 130 may be placed on either side of the body. For example, wrist sensor unit 126 may be placed on the non-dominant wrist, instead of the dominant wrist. Additional sensor units may be used to detect motion of other body segments. Each sensor unit 126, 128, 130 may have sensors that measure acceleration in different directions, up to a total of three orthogonal directions, X, Y, and Z, of a body segment, as in a typical physical-activity monitoring system, or it may have heart-rate sensors, temperature sensors, microphones, video sensors, or other types of sensors. Each sensor unit (sensor unit 126, 128, or 130) contains local clock 50, which is used to timestamp the acquired and stored sensor data for time synchronization. FIG. 12 is a block diagram illustrating the incorporation of a microphone 138 in wrist sensor unit 126 to record voice data, and wrist sensor unit 126 can act as a voice-recording wristwatch in addition to a physical-activity sensor. In FIG. 12, local clock 50 of wrist sensor unit 126 is also used to timestamp each segment of voice data obtained from microphone 138. The analog voice signal from microphone 138 is converted to digital voice data by a sample-and-hold circuit 140 and an analog-to-digital converter 144, and the timestamped digital voice-data segment is stored in a voice-data memory 142 by sensor-data controller 48. Data processor 70 receives the data stored in voice-data memory 142 through communication-link hub 80 for time synchronization of each voice-data segment with other timestamped sensor data. A user interface 146 facilitates the use of the voice-recording function of wrist sensor unit 126 by the human being to verbally clarify any type of physical activity that is difficult for the limited number of sensor units placed on the body to detect.

Figure 13:
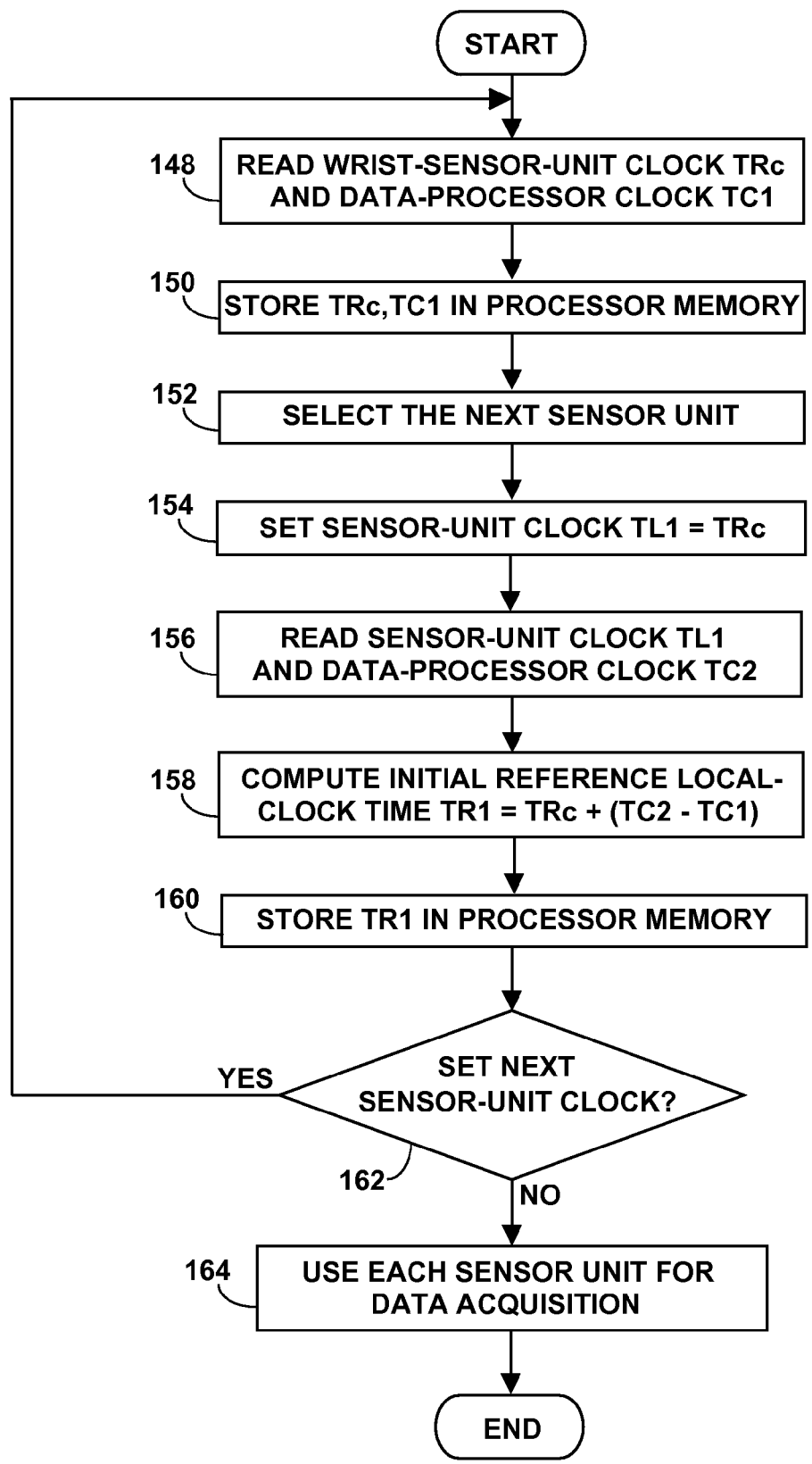
FIG. 13 is a flow diagram illustrating the synchronization operation of the data processor before a data-collection session in accordance with the second embodiment.
Figure 14:
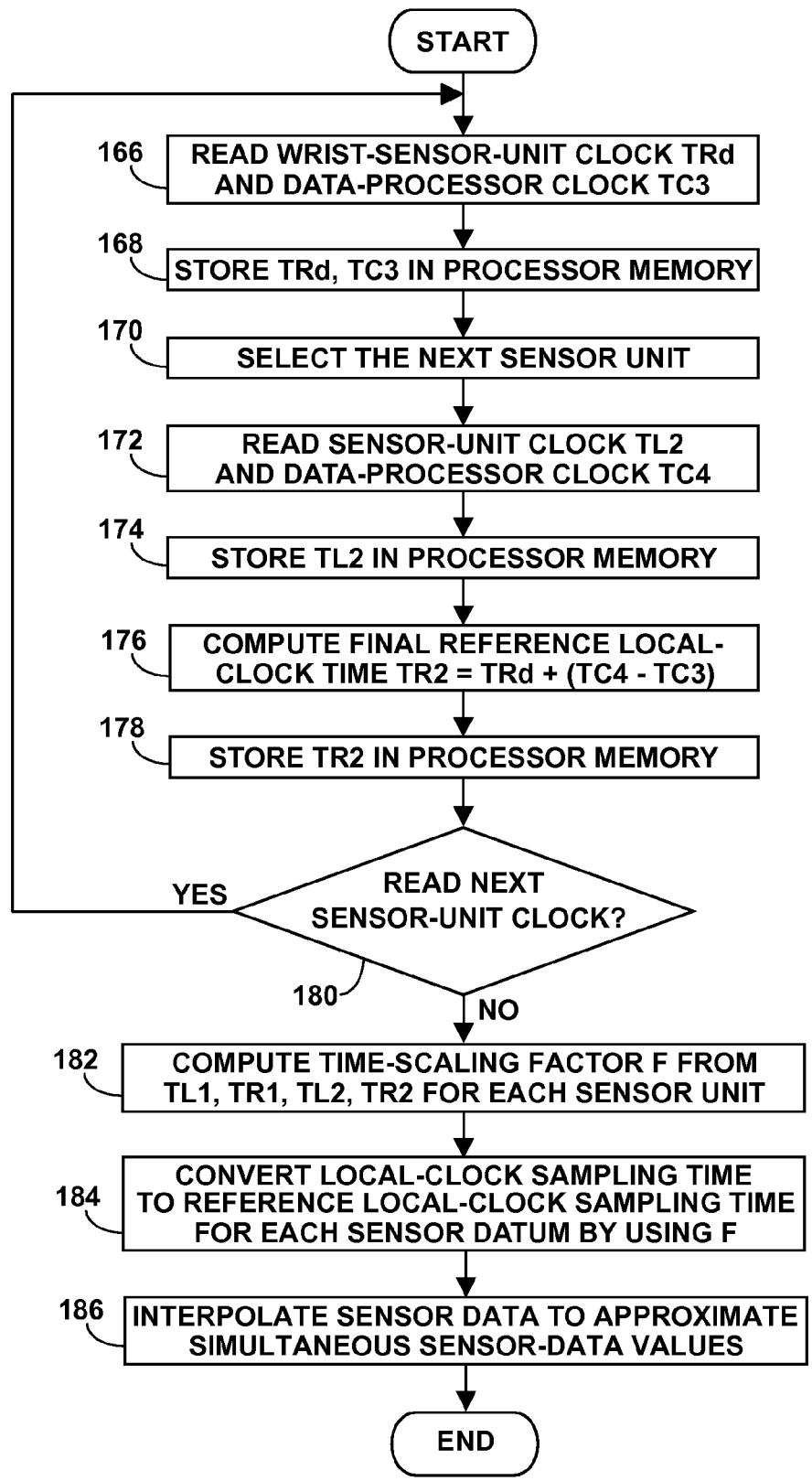
FIG. 14 is a flow diagram illustrating the synchronization operation of the data processor after a data-collection session in accordance with the second embodiment.

Synchronization Operation—FIGS. 13 and 14

When data processor 70 in the synchronization system is incorporated in wrist sensor unit 126, the synchronization operation of this embodiment is similar to that of the first embodiment, because the wrist sensor unit's reference local clock can be used by data processor 70 as the data processor's reference local clock. In this case, the communication between data processor 70 and wrist sensor unit 126 can be through direct electrical connections, instead of through communication-link hub 80. However, data processor 70 is usually separate from wrist sensor unit 126. In this case, the synchronization operation, using the wrist sensor unit's local clock as the reference local clock, can be performed as below.

FIG. 13 is a flow diagram for the synchronization operation before a data-collection session. Before a data-collection session, sensor units 126, 128, 130 communicate with data processor 70 through communication-link hub 80 to synchronize the local clocks of sensor units 128, 130 with the reference local clock of wrist sensor unit 126. Data processor 70 reads the wrist sensor unit's reference local-clock time TRc and the data processor's local-clock time TC1 at step 148, and data processor 70 stores TRc and TC1 in processor memory 66 (FIG. 3) at step 150. At step 152, data processor 70 selects the next sensor unit. Data processor 70 sends the reference local-clock time TRc to the selected sensor unit to set the sensor unit's initial local-clock time TL1 equal to the reference local-clock time TRc at step 154, and data processor 70 immediately reads back the sensor unit's initial local-clock time TL1 at step 156. At step 156, when data processor 70 receives the initial local-clock time TL1 through communication-link hub 80, it reads the data processor's current local-clock time TC2. At step 158, data processor 70 computes the initial reference local-clock time TR1 of wrist sensor unit 126 from the following equation, $$TR1=TRc+(TC2-TC1)=TL1+Td$$

where Td is the total elapsed time for data processor 70 to set the sensor-unit's initial local-clock time TL1 equal to TRc and then to read the initial local-clock time TL1 back from the sensor unit through the communication links, including through communication-link hub 80 and communication ports 54, 65 (FIGS. 3 and 10).

Data processor 70 stores TR1 in processor memory 66 at step 160. At step 162, data processor 70 selects the next sensor unit to repeat the clock-synchronization process, until each sensor unit 128, 130 has been selected. The initial reference local-clock time TR1 and the initial local-clock time TL1 (i.e. TRc, since TL1=TRc) for each sensor unit 128, 130 are stored in processor memory 66. After the clock-synchronization process, the local clocks of sensor units 128, 130 are set to about the same time, but the local-clock times are delayed from the wrist sensor unit's reference local-clock time by a time delay Td, as discussed in the following. By the time data processor 70 receives the reference local-clock time TRc from wrist sensor unit 126, the reference local-clock time of wrist sensor unit 126 will have already advanced to TRc+Tdu, where Tdu is the amount of time for sending a local-clock time from a sensor unit (sensor unit 126, 128, or 130) to data processor 70. Likewise, by the time data processor 70 receives the initial local-clock time TL1 (TL1 is set equal to TRc) from a sensor unit (sensor unit 128 or 130), the sensor unit's current local-clock time will have already advanced to TL1+Tdu, and the wrist sensor unit's current reference local-clock time will have further advanced to TRc+Tdu+Td. After the clock-synchronization process, the difference between the current reference local-clock time and the current local-clock time is $$(TRc+Tdu+Td)-(TL1+Tdu)=Td$$

The difference between the current reference local-clock time and the initial reference local-clock time TR1 (stored in processor memory 66) is $$(TRc+Tdu+Td)-(TL1+Td)=Tdu$$

Similarly, the difference between the current local-clock time and the initial local-clock time TL1 (stored in processor memory 66) is $$(TL1+Tdu)-TL1=Tdu$$

Although the current local-clock times of sensor units 128, 130 after the clock-synchronization process are delayed from the wrist sensor unit's current reference local-clock time by Td, TR1 and TL1 (both are stored in processor memory 66) are different from the current reference local-clock time and the current local-clock time, respectively, by the same amount of time delay Tdu.

FIG. 14 is a flow diagram for the synchronization operation after a data-collection session. After a data-collection session, sensor units 126, 128, 130 resume communication with data processor 70 through communication-link hub 80 (FIG. 11). Data processor 70 reads the wrist sensor unit's reference local-clock time TRd and the data processor's local-clock time TC3 at step 166, and data processor 70 stores TRd and TC3 in processor memory 66 at step 168. At step 170, data processor 70 selects the next sensor unit. Data processor 70 reads the final local-clock time TL2 from the selected sensor unit and the data processor's current local-clock time TC4 at step 172, and data processor 70 stores TL2 in processor memory 66 at step 174. At step 176, data processor 70 computes the final reference local-clock time TR2 from the following equation, $$TR2=TRd+(TC4-TC3)=TRd+Tdr$$

where Tdr is the total elapsed time for data processor 70 to request and receive the final local-clock time TL2 from the sensor unit through the communication links, including through communication-link hub 80 and communication ports 54, 65 (FIGS. 3 and 10).

Data processor 70 stores TR2 in processor memory 66 at step 178. At step 180, data processor 70 selects the next sensor unit to repeat this process, until each sensor unit 128, 130 has been selected. The final reference local-clock time TR2 and the final local-clock time TL2 of each sensor unit 128, 130 are stored in processor memory 66. By the time data processor 70 receives the reference local-clock time TRd from wrist sensor unit 126, the reference local-clock time of wrist sensor unit 126 will have already advanced to TRd+Tdu, where Tdu is the amount of time for sending a local-clock time from a sensor unit (sensor unit 126, 128, or 130) to data processor 70. Likewise, by the time data processor 70 receives the final local-clock time TL2, the current local-clock time of the sensor unit will have already advanced to TL2+Tdu, and the current reference local-clock time of wrist sensor unit 126 will have further advanced to TRd+Tdu+Tdr. The difference between the current reference local-clock time and the current local-clock time, taking into account the processes described above, is $$(TRd+Tdu+Tdr)-(TL2+Tdu)=(TRd-TL2)+Tdr$$

The difference between the current reference local-clock time and the final reference local-clock time TR2 (stored in processor memory 66) is $$(TRd+Tdu+Tdr)-(TRd+Tdr)=Tdu$$

Similarly, the difference between the current local-clock time and the final local-clock time TL2 (stored in processor memory 66) is $$(TL2+Tdu)-TL2=Tdu$$

The above results show that TR2 and TL2 (both stored in processor memory 66) are different from the current reference local-clock time and the current local-clock time, respectively, by the same amount of time delay Tdu. At step 182, a time-scaling factor F is computed from the following equation, $$F=(TR2-TR1)/(TL2-TL1)$$

For wrist sensor unit 126, F=1, because its local clock serves as the reference local clock. Since only the time differences TR2−TR1 and TL2−TL1 are used for computing F, F is an accurate time-scaling factor, because TR1, TR2, TL1, and TL2 are different from their corresponding current clock times by the same amount of time delay Tdu, as shown above. F is used to convert any local-clock time difference to its corresponding reference local-clock time difference, so that the reference local-clock sampling times can be computed from the local-clock sampling times.

When the stored data samples of a sensor unit (sensor unit 126, 128, or 130) are sent to data processor 70 (this process is not shown in FIG. 14), at least one of these data samples has a timestamp from the sensor unit's local clock. If a regular local-clock time interval TLi is used for data acquisition, the local-clock timestamp TLb of a data sample, usually the first data sample in a data-collection session, can be used to compute the local-clock sampling times of all the data in a sequence of sensor data. Data processor 70 converts the local-clock timestamp TLb to the reference-clock timestamp TRb as follows:

$$TRb=TR1+(TLb-TL1)\times F$$

In the above equation, the local-clock time difference TLb−TL1 is multiplied by the time-scaling factor F to convert it to its corresponding reference local-clock time difference.

TLi is also converted to the reference local-clock time interval by multiplying TLi with the time-scaling factor F, so that the reference local-clock sampling time TRs for each datum can be obtained as follows:

$$TRs=TRb+TLi\times F\times N$$

where N is the number of sampling intervals away from the reference local-clock timestamp TRb, and N is zero for the datum with timestamp TRb. N is a positive integer for data sampled after TRb, and it is a negative integer for data sampled before TRb.

After data processor 70 converts the local-clock sampling times to their corresponding reference local-clock sampling times for the data of all the sensor units, data processor 70 uses a data-interpolation technique, such as low-pass filtering with a finite-impulse-response (FIR) filter or linear interpolation between consecutive data samples, to interpolate the sensor data to approximate simultaneous sensor-data values at the desired reference local-clock times. In some cases, such as low-pass filtering of a band-limited signal, the approximation may be exact.

When setting the initial local-clock time TL1 of sensor units 128, 130 equal to the reference local-clock time TRc of wrist sensor unit 126 is not required, the synchronization process can be simplified. In this case, data processor 70 can sequentially read the initial reference local-clock time TR1 from wrist sensor unit 126 and the initial local-clock times TL1 from sensor units 128, 130 through communication-link hub 80 before a data-collection session. After the data-collection session, data processor 70 sequentially reads the final reference local-clock time TR2 from wrist sensor unit 126 and the final local-clock times TL2 from sensor units 128, 130 through communication-link hub 80, in the same reading order as the reading order before the data-collection session. The time-scaling factor F is equal to (TR2−TR1)/(TL2−TL1). Since only the time differences TR2−TR1 and TL2−TL1 are used for computing F, F is an accurate time-scaling factor if the time delays for reading the local-clock times of sensor units 126, 128, 130 sequentially by data processor 70 through the communication links, including through communication-link hub 80 and communication ports 54, 65 (FIGS. 3 and 10), are small, even though local clock 62 of data processor 70 is not used for estimating the time delays.

Syntonization Operation—FIG. 8

The syntonization operation of the second embodiment is similar to that of the first embodiment. Data processor 70 uses the time-scaling factor F to compute each sensor unit's local-clock frequency drift by using the wrist sensor unit's local-clock frequency as the reference. The computed frequency-adjustment data is used to adjust the frequency of the sensor unit's local clock, so that it matches the frequency of the reference local clock of wrist sensor unit 126 more closely.

Figure 15:
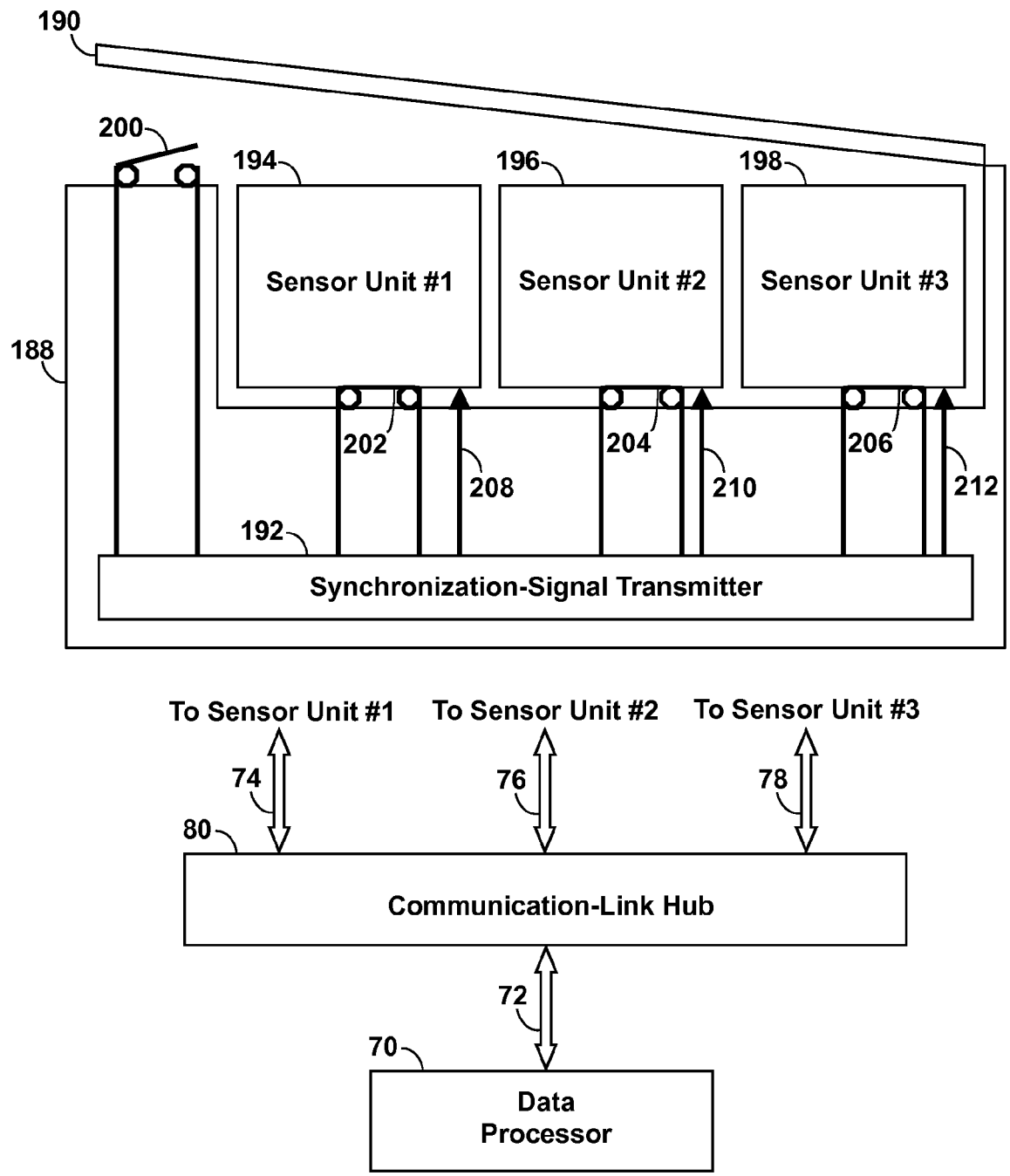
FIG. 15 illustrates schematically a mechanism for producing and transmitting a synchronization signal to three sensor units simultaneously before and after a data-collection session, in accordance with the third embodiment.
Figure 16:
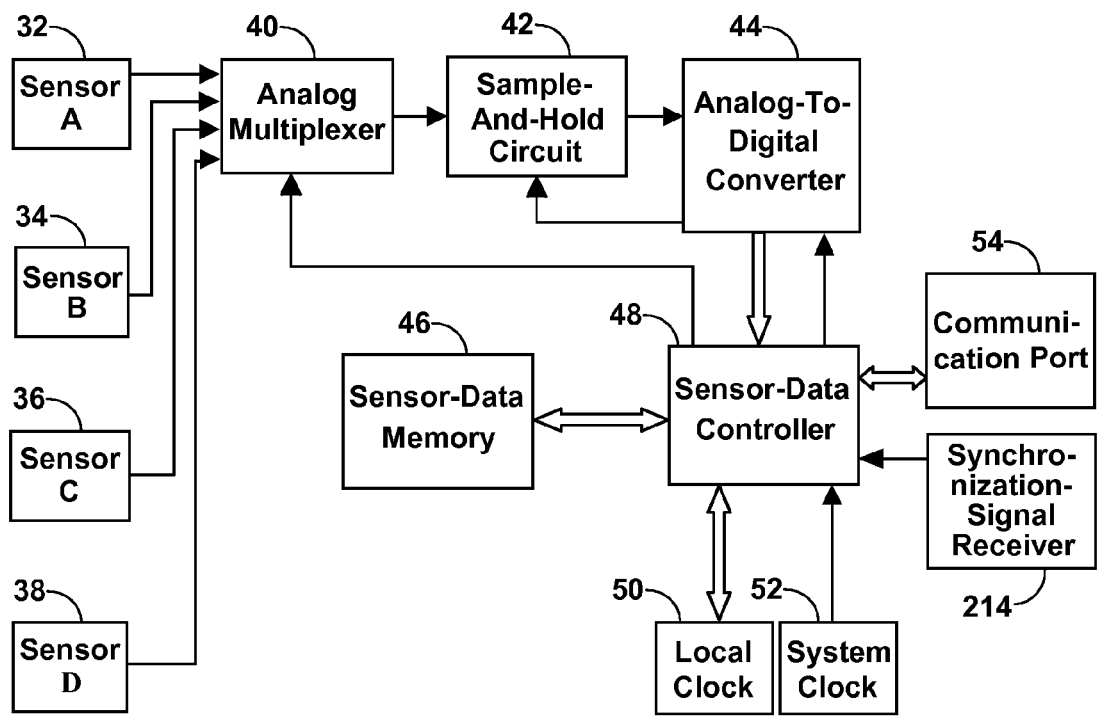
FIG. 16 is a block diagram showing schematically a sensor unit incorporating a synchronization-signal receiver in accordance with the third embodiment.
Figure 17:
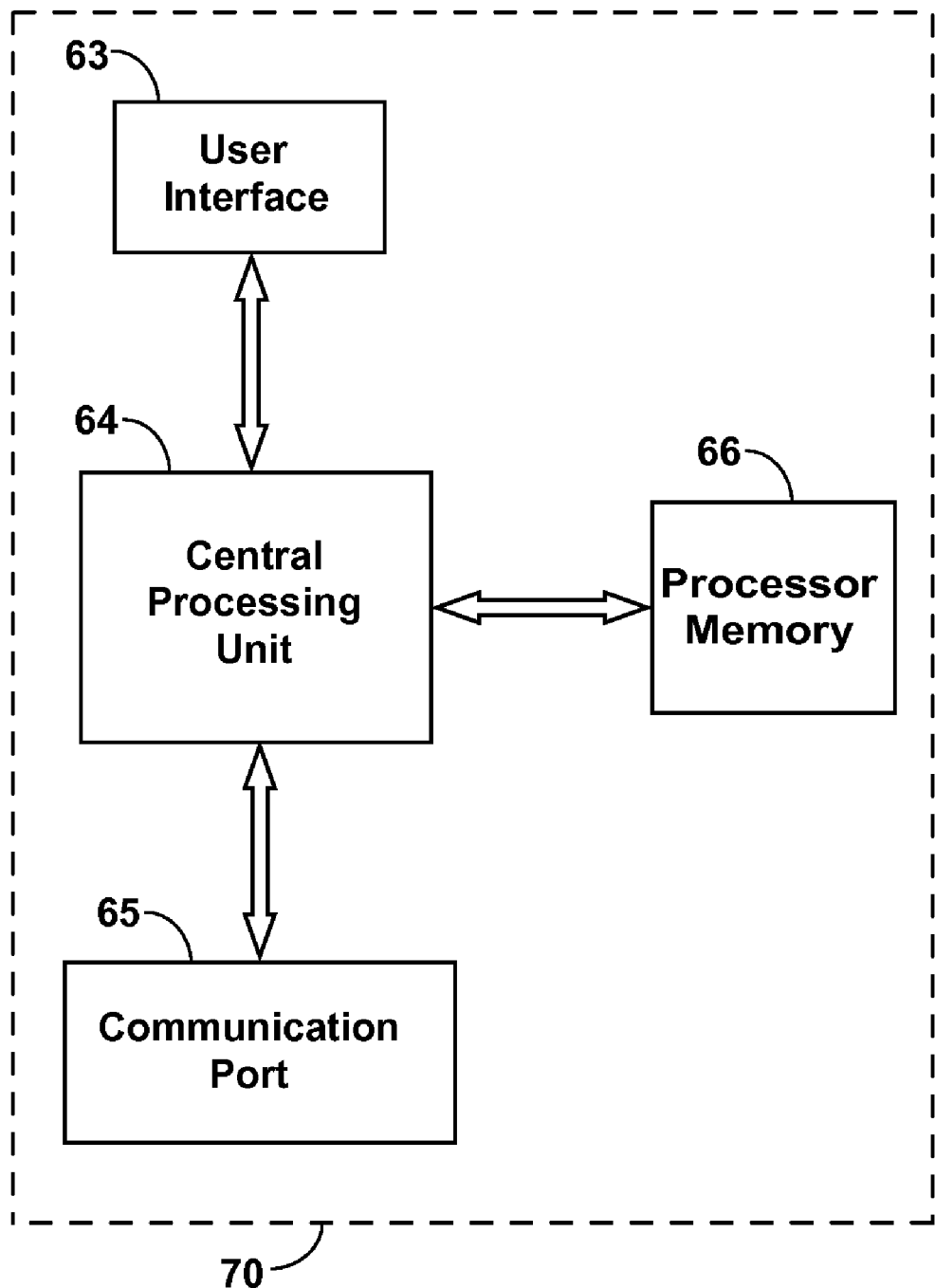
FIG. 17 is a block diagram showing schematically the data processor in accordance with the third embodiment.

FIGS. 15, 16 and 17—Third Embodiment

A third embodiment of the post data-collection synchronization system is illustrated in FIGS. 15, 16, and 17. This embodiment is similar to the second embodiment in that a sensor unit's local clock serves as the reference local clock, so that a local clock is not required in the data processor. In this embodiment, a synchronization-signal transmitter transmits a synchronization signal to all of the sensor units simultaneously before and after a data-collection session, so that the initial and final local-clock times are stored locally in the sensor units simultaneously and are sent to the data processor after the data-collection session. The data processor may use the local-clock times of any one of the sensor units as the reference local-clock times for the post data-collection synchronization.

FIG. 15 illustrates schematically a mechanism for producing and transmitting a synchronization signal to three sensor units simultaneously before and after a data-collection session, so that post data-collection synchronization can be achieved without needing to consider the time delays through the communication links, including through communication-link hub 80 and the communication ports of the data processor and the sensor units. Without needing to consider the time delays of the communication links and with any one of the sensor units' local clocks able to serve as the reference local clock, the time-synchronization operation is simplified and more accurate. Although three sensor units 194, 196, 198 (Sensor Unit #1, Sensor Unit #2, Sensor Unit #3, respectively) are shown in FIG. 15, a different number of sensor units may be used in the third embodiment. FIG. 16 illustrates schematically a block diagram of a sensor unit (sensor unit 194, 196, or 198). The operation of each sensor unit 194, 196, 198 is essentially the same as the operation of the sensor unit of the first embodiment, except that each sensor unit 194, 196, 198 incorporates a synchronization-signal receiver 214, so that a local-clock time can be stored in sensor-data memory 46 by sensor-data controller 48 when synchronization-signal receiver 214 receives a synchronization signal. FIG. 17 is a block diagram of data processor 70 of the third embodiment, which is the same as the block diagram of the data processor of the first embodiment, except that a local-clock is not used in data processor 70 for the synchronization operation.

In FIG. 15, sensor units 194, 196, 198 are stored in a container 188 before a data-collection session, and electrical switches 202, 204, 206 at the bottom of container 188 are closed because of the presence of sensor units 194, 196, 198. An electrical switch 200 at the top of container 188 is open when a lid 190 of container 188 is open. Although three sensor units are shown in FIG. 15, a different number of sensor units may be used. Furthermore, other types of switches such as optical switches or magnetic switches can be used to perform the switching function of switches 200, 202, 204, 206. Switch 200 at the top of container 188 is closed when lid 190 of container 188 is closed, but switch 200 opens (as shown in FIG. 15) when the user opens lid 190, so that sensor units 194, 196, 198 can be removed from container 188 for data acquisition. A synchronization-signal transmitter 192, which includes a logic circuit and a signal transmitter, is incorporated in container 188. It detects the opening of switch 200 at the top of container 188 while switches 202, 204, 206 at the bottom of container 188 are closed, and subsequently produces and transmits an initial synchronization signal through synchronization-signal links 208, 210, 212 simultaneously. Synchronization-signal links 208, 210, 212 can be simply electrical connections to sensor units 194, 196, 198. Upon reception of the initial synchronization signal, sensor units 194, 196, 198 store their local-clock times in their sensor-data memories as the initial local-clock times. When sensor units 194, 196, 198 are removed from container 188, switches 202, 204, 206 at the bottom of container 188 open.

After a data-collection session, when sensor units 194, 196, 198 return to container 188 for sending the collected data to data processor 70, switches 202, 204, 206 at the bottom of container 188 close again. Switch 200 at the top of container 188 is also closed when lid 190 closes, and synchronization-signal transmitter 192 in container 188 detects the closing of switch 200 at the top of container 188 while switches 202, 204, 206 at the bottom of container 188 are closed, subsequently producing and transmitting a final synchronization signal through synchronization-signal links 208, 210, 212 to sensor units 194, 196, 198 simultaneously. Upon reception of the final synchronization signal, sensor units 194, 196, 198 store their local-clock times in their sensor-data memories as the final local-clock times. Afterwards, the sensor data and the initial and final local-clock times of each sensor unit 194, 196, 198 are sent to data processor 70 through communication links 72, 74, 76, 78 and communication-link hub 80 for processing.

If communication link 72 is a wireless communication link that can facilitate direct communication between data processor 70 and each sensor unit 194, 196, 198 before and after a data-collection session, then communication-link hub 80 is not needed. Communication links 72, 74, 76, 78 may be the same type or different types of communication link, and they may be wired or wireless communication links, such as electrical, optical, acoustic, magnetic, or electromagnetic data links, etc., with corresponding communication ports in data processor 70 and sensor units 194, 196, 198. Although, not shown in FIG. 15, communication-link hub 80 or container 188 can also provide electrical power to charge the batteries in sensor units 194, 196, 198, so that wired or wireless communication using communication port 54 (FIG. 16) before or after a data-collection session does not drain energy from the batteries.

Instead of incorporating synchronization-signal transmitter 192 in container 188, synchronization-signal transmitter 192 can alternatively be incorporated in communication-link hub 80 or in data processor 70, or synchronization-signal transmitter 192 can be incorporated as a separate module. The functions of synchronization-signal transmitter 192 may also be incorporated in communication-link hub 80 or data processor 70, so that a dedicated synchronization-signal transmitter is not required. For example, communication-link hub 80 can incorporate devices for sensing the opening and closing statuses of switches 200, 202, 204, 206 in container 188. Communication-link hub 80 can send the statuses of switches 200, 202, 204, 206 to data processor 70 for performing the necessary logic functions, and then data processor 70 can send commands to communication-link hub 80, which in turn produces and transmits an initial or final synchronization signal through synchronization-signal links 208, 210, 212 to sensor units 194, 196, 198 simultaneously. Alternatively, data processor 70 can establish communication with each sensor unit 194, 196, 198 through communication-link hub 80 and communication links 72, 74, 76, 78 (FIG. 15) before and after a data-collection session to perform the initial and final synchronization processes, respectively. When communication with sensor units 194, 196, 198 is confirmed, data processor 70 can produce and transmit an initial or final synchronization signal, either directly or indirectly through communication-link hub 80, to sensor units 194, 196, 198 simultaneously at the beginning or the end of a data-collection session, respectively.

The logic circuit in synchronization-signal transmitter 192 for automatically detecting the beginning and the end of a data-collection session is not required if the user can follow instructions to turn on an electrical switch to cause synchronization-signal transmitter 192 to transmit an initial synchronization signal at the beginning of a data-collection session and a final synchronization signal at the end of a data-collection session. For example; turning on the electrical switch briefly can cause synchronization-signal transmitter 192 to transmit an initial synchronization signal, and turning on the electrical switch for a longer period of time can cause synchronization-signal transmitter 192 to transmit a final synchronization signal. Instead of using different turn-on durations of the electrical switch, other protocols such as using different turn-on frequencies of the switch or using two different switches can be employed for causing synchronization-signal transmitter 192 to transmit the initial and final synchronization signals. The initial and final synchronization signals may be electrical, magnetic, electromagnetic, optical, acoustic, or mechanical, with a corresponding synchronization-signal receiver in each sensor unit 194, 196, 198. The initial synchronization signal may differ from the final synchronization signal by pulse length, pulse height, pulse frequency, or any other signal parameters, or by the means or the paths of signal transmission. For example, the initial synchronization signal may be transmitted magnetically while the final synchronization signal may be transmitted optically.

Figure 18:
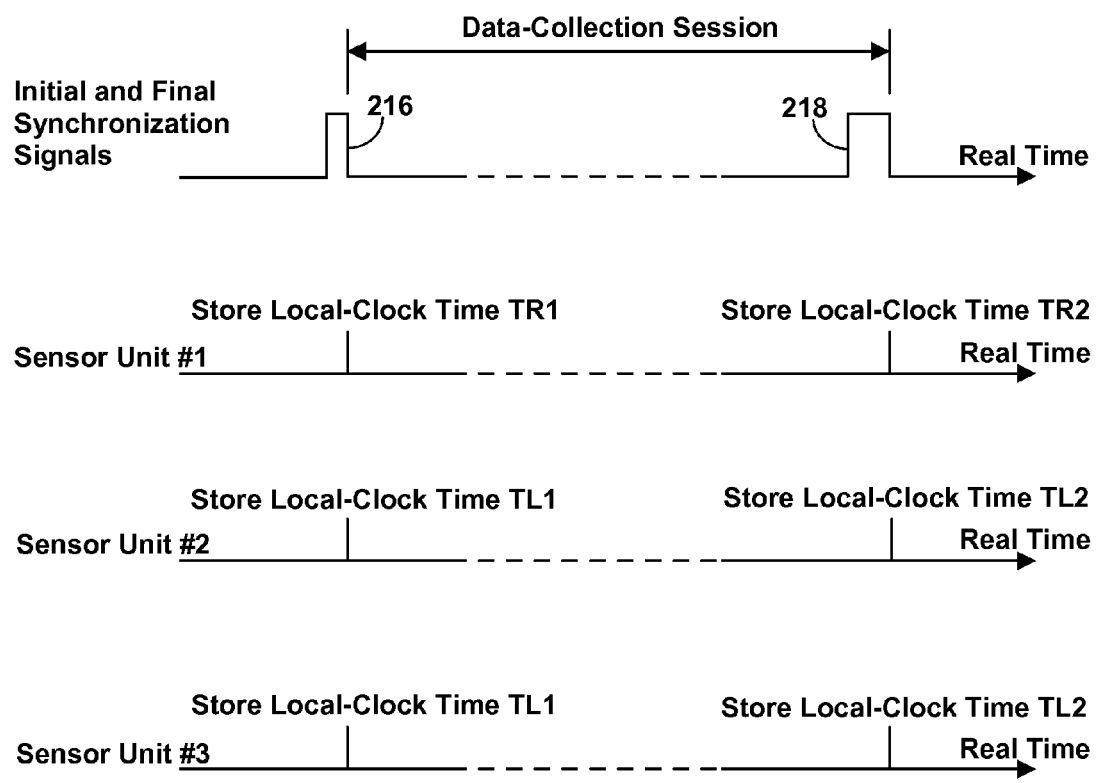
FIG. 18 is a timing diagram illustrating storing of the initial and final local-clock times in three sensor units simultaneously upon receiving the initial and final synchronization signals, respectively, in accordance with the third embodiment.
Figure 19:
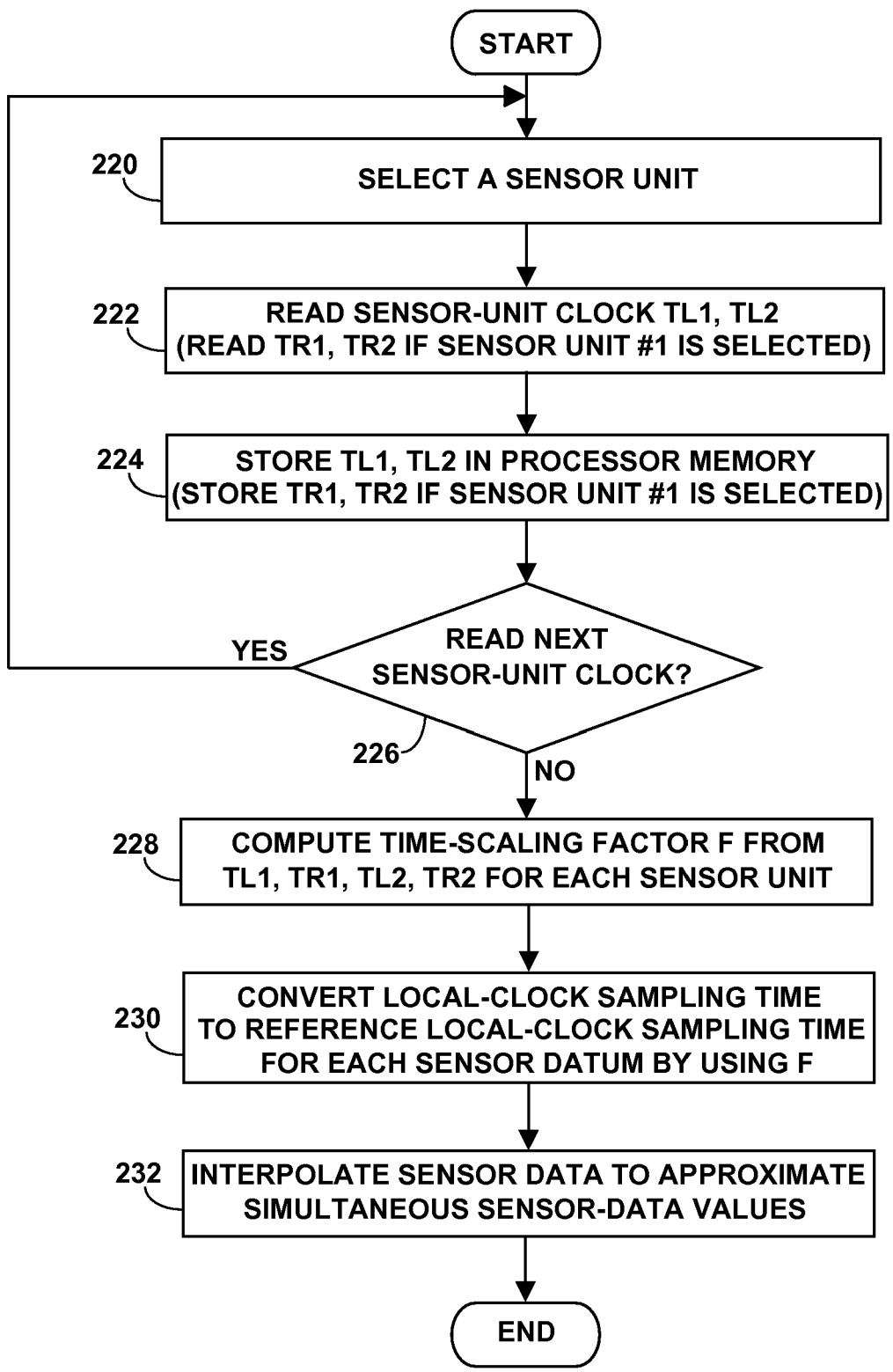
FIG. 19 is a flow diagram illustrating the synchronization operation of the data processor in accordance with the third embodiment.

Synchronization Operation—FIGS. 18 and 19

FIG. 18 is a timing diagram illustrating storing of the initial and final local-clock times in sensor units 194, 196, 198 (Sensor Unit #1, Sensor Unit #2, Sensor Unit #3, respectively, in FIG. 15) simultaneously when sensor units 194, 196, 198 receive the initial and final synchronization signals, and the local clock of sensor unit 194 (Sensor Unit #1) serves as the reference local clock. Although the local clock of sensor unit 194 is selected as the reference local clock for illustrating the synchronization operation, the local clock of sensor unit 196 or 198 may also serve as the reference local clock. In FIG. 18, a final synchronization signal 218 differs from an initial synchronization signal 216 by its longer pulse length. When sensor units 194, 196, 198 are not in use, they are stored in container 188 with lid 190 closed. Before a data-collection session, sensor units 194, 196, 198 are removed from container 188. At the instant that lid 190 of container 188 is opened for removing sensor units 194, 196, 198, synchronization-signal transmitter 192 transmits initial synchronization signal 216 through synchronization-signal links 208, 210, 212 (FIG. 15) to sensor units 194, 196, 198 simultaneously. Upon reception of initial synchronization signal 216, sensor unit 194 (Sensor Unit #1) stores its initial reference local-clock time TR1 and sensor units 196, 198 (Sensor Unit #2, Sensor Unit #3, respectively) store their initial local-clock times TL1 in their sensor-data memories at the same time. After the initial synchronization process, sensor units 194, 196, 198 (Sensor Unit #1, Sensor Unit #2, Sensor Unit #3, respectively) are removed from container188 and used for data acquisition without any communication with data processor 70 or among themselves.

After a data-collection session, sensor units 194, 196, 198 (Sensor Unit #1, Sensor Unit #2, Sensor Unit #3, respectively) return to container 188. At the instant that lid 190 of container 188 closes, synchronization-signal transmitter 192 transmits final synchronization signal 218 through synchronization-signal links 208, 210, 212 to sensor units 194, 196, 198 (Sensor Unit #1, Sensor Unit #2, Sensor Unit #3, respectively) simultaneously. Upon reception of final synchronization signal 218, sensor unit 194 (Sensor Unit #1) stores its final reference local-clock time TR2, and sensor units 196, 198 (Sensor Unit #2, Sensor Unit #3, respectively) store their final local-clock times TL2 in their sensor-data memories at the same time.

FIG. 19 is a flow diagram for illustrating the synchronization operation of data processor 70 after data collection. After a data-collection session, each sensor unit 194, 196, 198 communicates with data processor 70 through communication-link hub 80. Data processor 70 selects a sensor unit at step 220 and read the sensor unit's initial and final local-clock times, TL1 and TL2 (or TR1 and TR2, if sensor unit 194 is selected), respectively, at step 222. At step 224, data processor 70 stores TL1 and TL2 (or TR1 and TR2, if sensor unit 194 is selected) in processor memory 66 (FIG. 17). At step 226, data processor 70 repeats this process for the next sensor unit, until each sensor unit 194, 196, 198 has been selected. At step 228, data processor 70 computes a time-scaling factor F for each sensor unit as follows:

$$F=(TR2-TR1)/(TL2-TL1)$$

For wrist sensor unit 194, F is equal to 1, since TR1=TL1 and TR2=TL2. Because of the differences in accuracy between the reference local clock of wrist sensor unit 194 and each of the local clocks of sensor units 196, 198, usually TR1 is not equal to TL1, and TR2 is not equal to TL2. Since only the time differences TR2−TR1 and TL2−TL1 are used for computing F, F is an accurate time-scaling factor, even though the clocks do not have the same reading. At step 230, F is used to convert any local-clock time difference to its corresponding reference local-clock time difference, so that the reference local-clock sampling times can be computed from the local-clock sampling times.

When the stored data samples of a sensor unit (sensor unit 194, 196, or 198) are sent to data processor 70 (this process is not shown in FIG. 19), at least one of these data samples has a timestamp from the sensor unit's local clock. If a regular local-clock time interval TLi is used for data acquisition, the local-clock timestamp TLb of a data sample, usually the first data sample in a data-collection session, can be used to compute the local-clock sampling times of all the data in a sequence of sensor data. The data processor converts the local-clock timestamp TLb to the reference-clock timestamp TRb as follows:

$$TRb=TR1+(TLb-TL1)\times F$$

In the above equation, the local-clock time difference TLb−TL1 is multiplied by the time-scaling factor F to convert it to the reference local-clock time difference.

TLi is also converted to the reference local-clock time interval by multiplying TLi with the time-scaling factor F, so that the reference local-clock sampling time TRs for each datum can be obtained as follows:

$$TRs=TRb+TLi\times F\times N$$

where N is the number of sampling intervals away from the reference local-clock timestamp TRb, and N is zero for the datum with timestamp TRb. N is a positive integer for data sampled after TRb, and it is a negative integer for data sampled before TRb.

After data processor 70 converts the local-clock sampling times to the reference local-clock sampling times for the data of sensor units 194, 196, 198, data processor 70 uses a data-interpolation technique, such as low-pass filtering with a finite-impulse-response (FIR) filter or linear interpolation between consecutive data samples, to interpolate the sensor data to approximate simultaneous sensor-data values at the desired reference local-clock times. In some cases, such as low-pass filtering of a band-limited signal, the approximation may be exact.

Syntonization Operation—FIG. 8

The syntonization operation of the third embodiment is similar to that of the first embodiment. Data processor 70 uses the time-scaling factor F to compute the local-clock frequency drift of sensor unit 196 or 198 by using the local-clock frequency of sensor unit 194 as the reference. The computed frequency-adjustment data is used to adjust the local-clock frequency of sensor unit 196 or 198, so that it matches the local-clock frequency of sensor unit 194 more closely.

Although the description above contains many specificities, these should not be construed as limiting the scope of the embodiments but as merely providing illustrations of some of the presently preferred embodiments. For example, the above-described embodiments can be modified by one skilled in the art, especially in the combination of various described features, without departing from the spirit and the scope of the embodiments.

Thus the scope of the embodiments should be determined by the appended claims and their legal equivalents, rather than by the examples given.

We claim:

1. A method for post data-collection synchronization of data of at least one sensor unit in a distributed sensor system, comprising:
    (a) reading an initial local-clock time of a sensor unit, having a local clock, by a data processor before a data-collection session;
    (b) reading an initial reference local-clock time of said data processor, having a reference local clock, by said data processor before the data-collection session;
    (c) reading a final local-clock time of said sensor unit by said data processor after the data-collection session;
    (d) reading a final reference local-clock time of said data processor by said data processor after the data-collection session;
    (e) computing a time-scaling factor by said data processor as the ratio of the difference between the final and initial reference local-clock times and the difference between the final and initial local-clock times;
    (f) converting at least two local-clock sampling times of said sensor unit's collected data from the data-collection session by said data processor to their corresponding reference local-clock sampling times using the time-scaling factor; and
    (g) interpolating said sensor unit's collected data from the data-collection session by said data processor to approximate a data value of said sensor unit at a reference local-clock time between said reference local-clock sampling times.

2. The method according to claim 1, further comprising:
    (a) computing a frequency difference between said local clock of said sensor unit and said reference local clock of said data processor using the time-scaling factor; and
    (b) adjusting the frequency of said local clock of said sensor unit to match the frequency of said reference local clock of said data processor more closely by using said frequency difference.

3. The method according to claim 1 further comprising collecting acceleration data from a body segment of a human being by said sensor unit during the data-collection session.

4. The method according to claim 3 wherein the local clock of said sensor unit is a wristwatch.

5. The method according to claim 4 wherein said sensor unit further comprising a voice recorder for recording the types of physical activity performed by the human being.

6. A method for post data-collection synchronization of data of a plurality of sensor units in a distributed sensor system, comprising:
    (a) reading an initial local-clock time of each sensor unit, having a local clock, of a plurality of sensor units by a data processor before a data-collection session;
    (b) reading a final local-clock time of each sensor unit of said plurality of sensor units by said data processor after the data-collection session;
    (c) computing a time-scaling factor for each sensor unit of said plurality of sensor unit sensor units by said data processor as the ratio of the difference between the final and initial local-clock times of a selected sensor unit of said plurality of sensor units and the difference between the final and initial local-clock times of said sensor unit;
    (d) converting at least two local-clock sampling times of collected sensor data from the data-collection session of each sensor unit of said plurality of sensor units by said data processor to their corresponding local-clock sampling times of said selected sensor unit using the time-scaling factor; and
    (e) interpolating the collected sensor data from the data-collection session of each sensor unit of said plurality of sensor unit by said data processor to approximate simultaneous sensor-data values of said plurality of sensor units at a time between said local-clock sampling times of said selected sensor unit.

7. The method according to claim 6, further comprising:
    (a) computing a frequency difference between the local clock of a sensor unit of said plurality of sensor units and the local clock of said selected sensor unit using the time-scaling factor; and
    (b) adjusting the frequency of the local clock of said sensor unit to match the frequency of the local clock of said selected sensor unit more closely by using said frequency difference.

8. The method according to claim 6 further comprising collecting acceleration data from a body segment of a human being by a sensor unit of said plurality of sensor units during the data-collection session.

9. The method according to claim 6, further comprising:
    (a) collecting acceleration data from a wrist of a human being by a wrist sensor unit of said plurality of sensor units during the data-collection session;
    (b) collecting acceleration data from the waist of the human being by a waist sensor unit of said plurality of sensor units during the data-collection session; and
    (c) collecting acceleration data from a thigh of the human being by a thigh sensor unit of said plurality of sensor units during the data-collection session.

10. The method according to claim 9 wherein the local clock of said wrist sensor unit is a wristwatch.

11. The method according to claim 10 wherein said wrist sensor unit further comprising a voice recorder for recording the types of physical activity performed by the human being.

12. A post data-collection synchronization system, comprising:
    (a) a plurality of sensor units, each sensor unit having a local clock, a synchronization-signal receiver for receiving synchronization signals, a sensor, a sensor-data controller for data acquisition from said sensor, a sensor-data memory for storing said sensor's data and said local clock's times, a communication port for sending said sensor's data and said local clock's times to a data processor, and a data-interpolating means for approximation of simultaneous sensor-data values of said plurality of sensor units after a data-collection session; and (b) a synchronization-signal transmitter for transmitting an initial synchronization signal to said synchronization-signal receiver of each sensor unit of said plurality of sensor units simultaneously before the data-collection session and a final synchronization signal to said synchronization-signal receiver of each sensor unit of said plurality of sensor units simultaneously after the data-collection session, so that said local clock's time of each sensor unit of said plurality of sensor units is stored in said sensor-data memory when one of said initial synchronization signal and said final synchronization signal is received by said synchronization-signal receiver.

13. The system according to claim 12 further comprising a means for adjusting the frequency of the local clock of a sensor unit of said plurality of sensor units.

14. The system according to claim 12 further comprising a container for placing said plurality of sensor units, so that said synchronization-signal transmitter can transmit said initial synchronization signal and said final synchronization signal to said plurality of sensor units at the beginning and the end of the data collection session, respectively.

15. The system according to claim 14 wherein said container further comprising:
(a) a lid; and
(b) a plurality of switches in said container for sensing closing and opening of said lid and presence and absence of said plurality of sensor units in said container, so that said synchronization-signal transmitter can transmit said initial synchronization signal and said final synchronization signal to said plurality of sensor units at the beginning and the end of the data collection session, respectively.

16. The system according to claim 12 wherein a sensor in a sensor unit of said plurality of sensor units is an accelerometer for monitoring acceleration of a body segment of a human being.

17. The system according to claim 12 wherein said plurality of sensor units comprising:
(a) a wrist sensor unit for collecting acceleration data from a wrist of a human being during the data-collection session;
(b) a waist sensor unit for collecting acceleration data from the waist of the human being during the data-collection session; and
(c) a thigh sensor unit for collecting acceleration data from a thigh of the human being during the data-collection session.

18. The system according to claim 17 wherein the local clock of said wrist sensor unit is a wristwatch.

19. The system according to claim 18 wherein said wrist sensor unit further comprising a voice recorder for recording the types of physical activity performed by the human being.

20. The system according to claim 12 further comprising a communication-link hub for providing communication between said data processor and each sensor unit of said plurality of sensor units.

* * * * *